(12) United States Patent
Shostak

(10) Patent No.: US 7,248,881 B2
(45) Date of Patent: *Jul. 24, 2007

(54) VOICE-CONTROLLED WIRELESS COMMUNICATIONS SYSTEM AND METHOD

(75) Inventor: Robert E. Shostak, Portola Valley, CA (US)

(73) Assignee: Vocera Communications, Inc., Cupertino, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 10/735,218

(22) Filed: Dec. 12, 2003

(65) Prior Publication Data

US 2004/0127241 A1    Jul. 1, 2004

Related U.S. Application Data

(60) Division of application No. 10/231,720, filed on Aug. 30, 2002, now Pat. No. 6,892,083, which is a continuation-in-part of application No. 09/947,235, filed on Sep. 5, 2001, now Pat. No. 6,901,255.

(51) Int. Cl.
    *H04Q 7/20* (2006.01)
(52) U.S. Cl. .................. 455/456.1; 455/563; 455/41.2
(58) Field of Classification Search ............... 455/41.2, 455/456.1, 41.3, 575.1, 566, 550.1, 556.1, 455/456.2, 456.5, 457, 90.3, 563
    See application file for complete search history.

(56) References Cited

U.S. PATENT DOCUMENTS

| 5,515,426 | A | 5/1996 | Yacenda et al. |
| 5,819,183 | A | 10/1998 | Voroba et al. |
| 5,960,366 | A | 9/1999 | Duwaer |
| 6,049,710 | A | 4/2000 | Nilsson |
| 6,150,951 | A | 11/2000 | Olejniczak |
| 6,215,992 | B1 | 4/2001 | Howell et al. |
| 2002/0168986 | A1* | 11/2002 | Lau et al. .................... 455/456 |
| 2003/0022696 | A1* | 1/2003 | Rosner ....................... 455/564 |

OTHER PUBLICATIONS

PCT Search Report dated Nov. 27, 2002 corresponding to PCT/US02/28096.
Written Opinion dated Jul. 15, 2003 corresponding to PCT/US02/28096.
PCT Search Report dated May 30, 2006 corresponding to the related PCT Patent Application US03/27374.

* cited by examiner

*Primary Examiner*—Lewis West
(74) *Attorney, Agent, or Firm*—DLA Piper US LLP

(57) ABSTRACT

A wireless communication system has a central computer, one or more wireless access points and one or more personal badges that communicate wirelessly with the one or more wireless access points. The badges provide the user with a communications device that permits the user to initiate telephone calls and conferences, receive telephone calls, receive pages and be located within a particular environment.

2 Claims, 10 Drawing Sheets

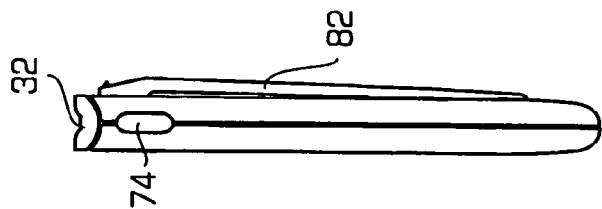
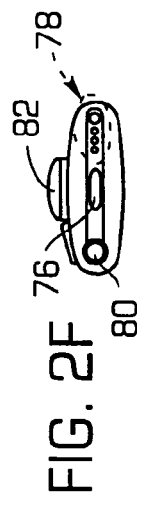
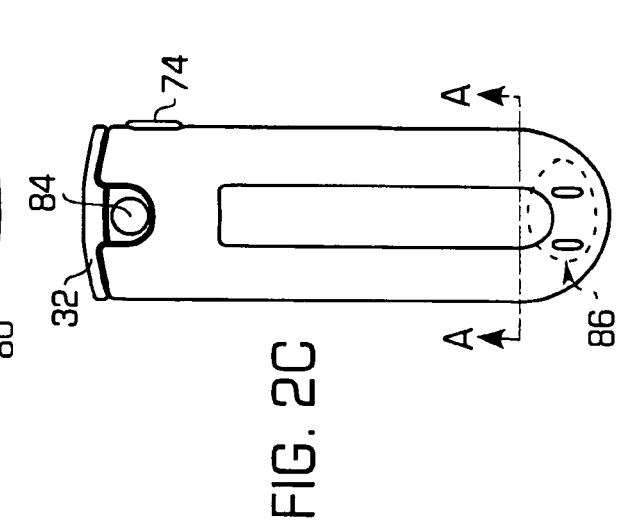
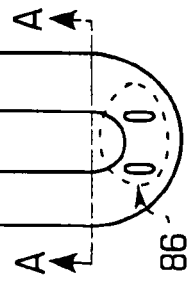
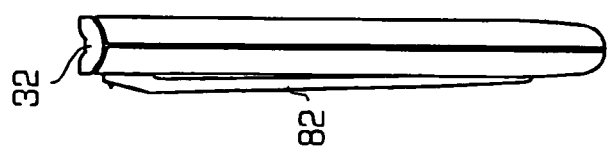
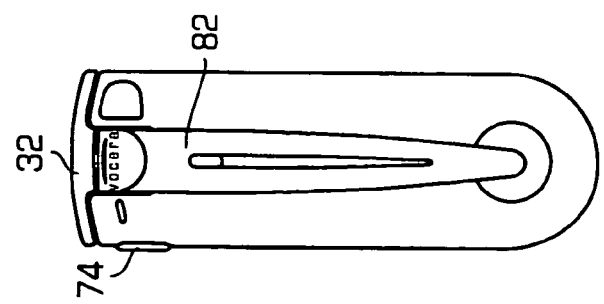

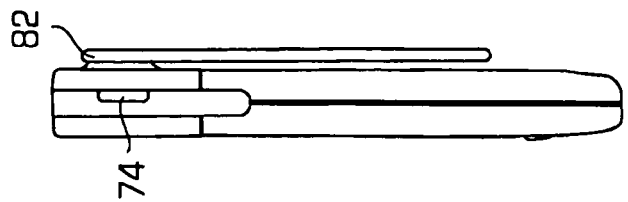
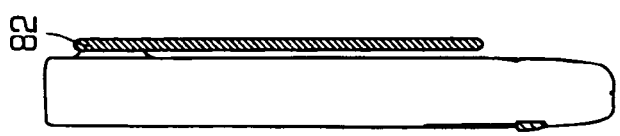
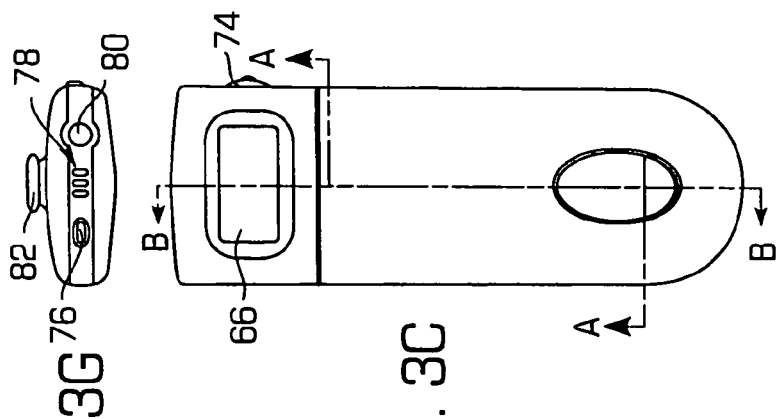
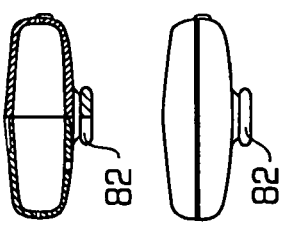
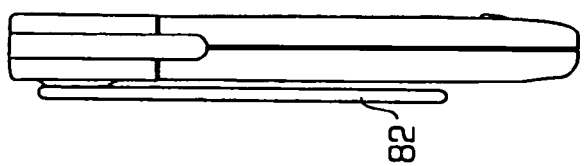
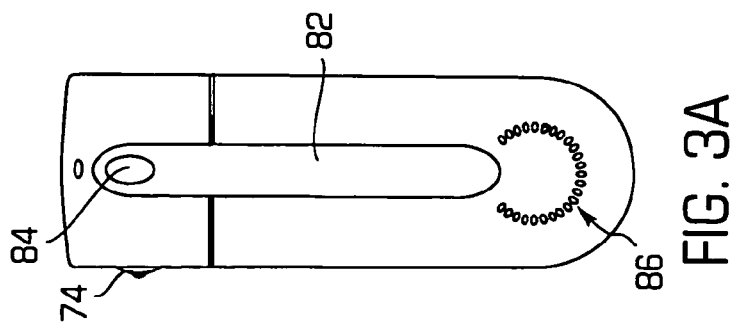

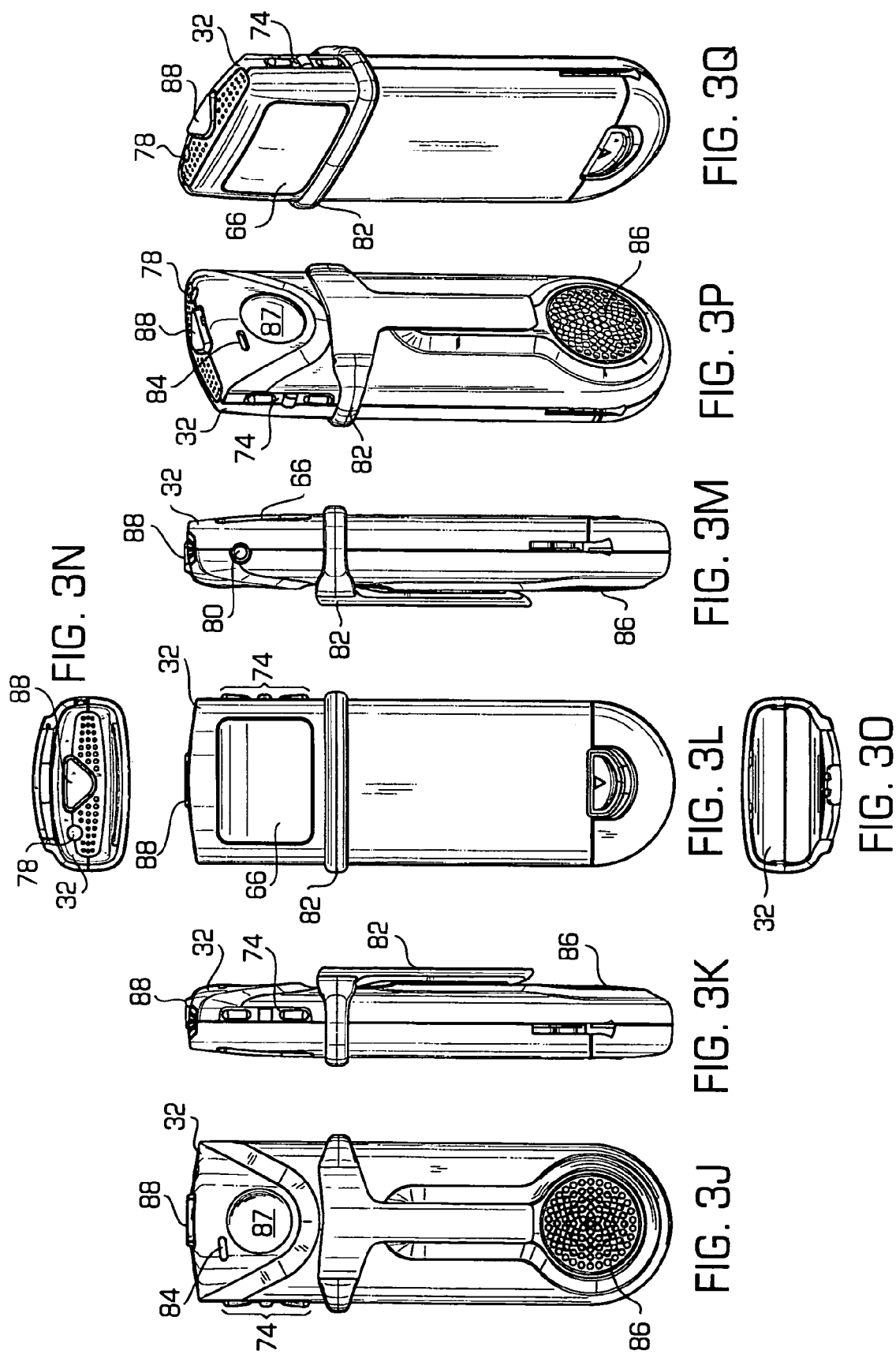

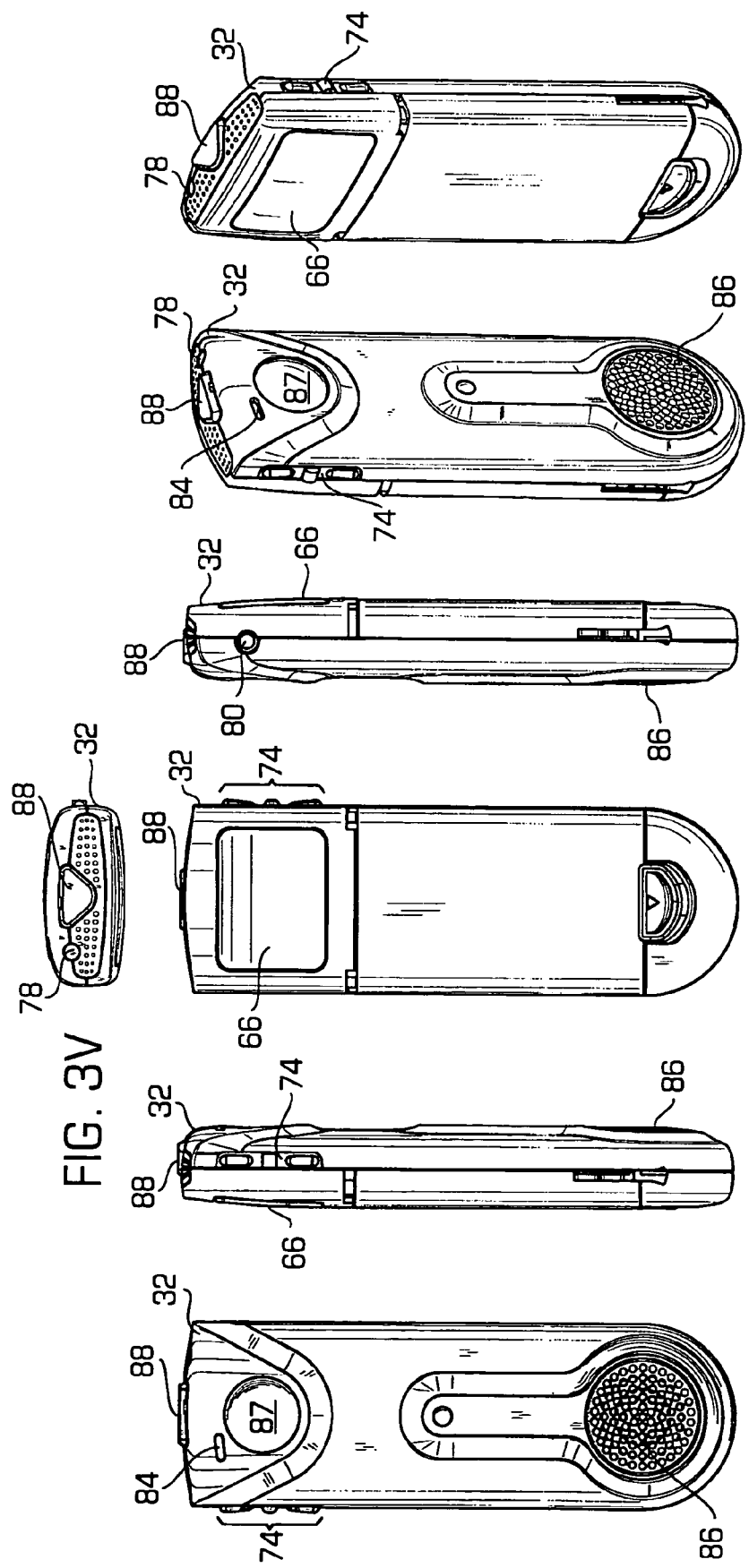

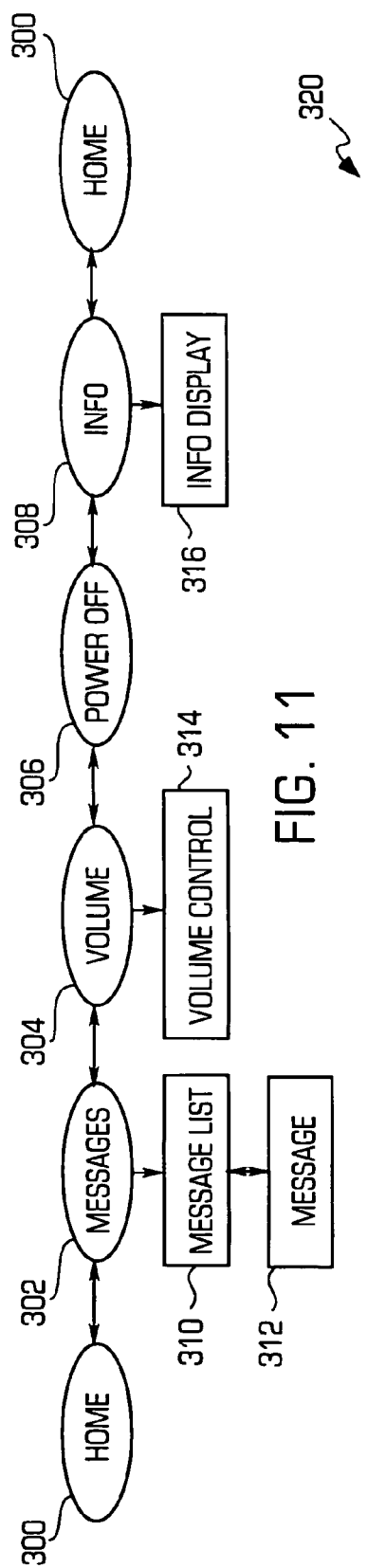

FIG. 11

| SCREEN | UP | DOWN | SELECT | SELECT AND HOLD |
|---|---|---|---|---|
| HOME | MESSAGES | INFO | HOME | HOME |
| MESSAGES | VOLUME | HOME | MESSAGE LIST | HOME |
| VOLUME | POWER OFF | MESSAGES | VOLUME ADJ. | HOME |
| POWER OFF | INFO | VOLUME | *POWER OFF* | HOME |
| INFO | HOME | POWER OFF | BADGE ID | HOME |
| MESSAGE LIST | *SCROLL UP* | *SCROLL DOWN* | MESSAGE | HOME |
| MESSAGE | *SCROLL UP* | *SCROLL DOWN* | MESSAGE LIST | HOME |
| VOLUME ADJUST | *VOL. UP* | *VOL. DOWN* | HOME | HOME |
| BADGE ID | VERSION | MAC ADDR | HOME | HOME |
| MAC ADDRESS | BADGE ID | VERSION | HOME | HOME |
| VERSION | MAC ADDR | SSID | HOME | HOME |
| SSID | VERSION | LOCATION | HOME | HOME |
| LOCATION | SSID | BADGE ID | HOME | HOME |

FIG. 12

VOICE-CONTROLLED WIRELESS COMMUNICATIONS SYSTEM AND METHOD

PRIORITY CLAIM

This application claims priority under 35 U.S.C. 120 to and is a divisional application of U.S. patent application Ser. No. 10/231,720, filed on Aug. 30, 2002 now U.S. Pat. No. 6,892,083 which claims priority under 35 USC 120 and is a continuation-in-part application of U.S. patent application Ser. No. 09/947,235, filed Sep. 5, 2001 now U.S. Pat. No. 6,901,255, entitled "Voice-Controlled Wireless Communications System and Method" and owned by the same assignee as the present invention.

APPENDICES

Attached hereto are: 1) Appendix A (15 pages) containing the user profile database record; and 2) Appendix B (10 pages) containing the system information database record.

BACKGROUND OF THE INVENTION

This invention relates generally to a system and method for providing wireless communications between individuals and in particular to a system and method that uses lightweight wireless devices that communicate with one ore more access points which in turn connect to a typical communications/computer network.

Various different wireless communication devices are well known and form a large part of our everyday lives. Examples of the well known wireless communication devices include cellular phones from various manufacturers, wireless e-mail systems, such as the Research in Motion (RIM) wireless e-mail devices that include personal information management features and capabilities, pages and other wireless access devices, such as Palm-type handheld devices that permit e-mail or Internet access.

These well known wireless communication devices provide an expanding range of capabilities. For example, when originally introduced, cellular phones provided only wireless telephone access and the clarity of the cellular phone calls was not clear. Recently, the next generation of cellular phones were introduced (2 G handsets) that provided limited Internet access so that, for example, a user may browse the World Wide Web as one might do with a typical desktop computer. The level of access, however, was very limited and unsatisfactory. These cellular phones typically provided some browsing capability, but nothing else due to various limitations including small display screen size and limited bandwidth connections. Recently, the next generation of cellular phones (2.5 G and 3 G handsets) are being introduced which allegedly will provide greater bandwidth connections that will enable the same level of functionality as is provided to a desktop computer.

Thus, these devices permit the integration of telephony functions with the functions of a web browser. Even the smallest cellular phones, however, are still fairly bulky and difficult to have available at all times, such as clipped to the shirt pocket of the user. The cellular phones also still do not have reliable communications since the footprint of the cells for the cellular phones is still being expanded to provide better coverage. However, none of these systems provide wireless, lightweight communications system that is voice activated and driven. Some known cellular phones provide some limited voice-recognition capability, such as to dial a phone number based on a name of a person, but do not provide a wide breadth of voice-activated functions in small, lightweight package. Thus, it is desirable to provide a voice-activated and driven wireless communications system. It would be desirable to provide a lightweight, highly portable user device that permits the user to interact with the system.

Most current wireless communication devices are not easy to use hands-free devices so that they, therefore, require the user to use his hands to hold and operate the device. Some cellular phones provide hands free units that permit the user to talk on the cellular phone without having to hold the cellular phone during the conversation. However, even with the hands free unit, the user must still dial the phone number or speak the phone number to initiate the call. Typically, to answer a call, the user must press a button. Thus, it is desirable to provide a voice-controlled wireless communications system that overcomes the limitations and drawbacks of typical wireless systems and it is to this end that the present invention is directed.

SUMMARY OF THE INVENTION

A voice-controlled wireless communications system is provided. The system may comprise a small, portable, lightweight user device for each user, one or more access points with which each user device communicates, and a central computer system that controls the communications wherein the central computer and the one or more access points are connected together by a typical computer/communications network, such as a local area network (LAN), a wide area network (WAN) or another similar network. In a preferred embodiment, the system may comprise a badge for each user, one or more access points that are spaced appropriately and one or more server computers that control the communications. In more detail, each badge is a battery powered transceiver that is capable of communicating with an adjacent access point in order to perform various different desirable functions, including calling another user, calling an outside person, receiving a call from a user or third party, determining the location of a user of the system, configuring the communications system, receiving a page from a third party and many others that are described in more detail below. Each badge has very limited computing power so that the bulk of the processing to execute the one or more commands of the user are implemented by the server and the badge operates as an access device that permits the user to access the functions and capabilities of the server as described below. Each access point has some limited communications range and can handle some predetermined number of active badges (an active badge is a badge that is currently actively engaged in a communication with the server or a third party). Thus, for a predetermined area, such as a office building or office complex, there are a plurality of access points that are spaced apart from each other so that all locations in the entire building/complex are within range of at least one access point. To permit handoff between the different access points, the coverage of each access point may overlap the coverage of another access point so that the communications session of a badge that is moving between coverage of different access points is not dropped. Since the badges are lightweight and do not have sufficient computer power to perform various functions, the server performs those functions, such as voice recognition and executing the various desirable functions of the wireless communications system in accordance with the invention.

Now, to briefly explain the operation of the system, an example of the execution of one command will be described. For example, to place a call to a third party or another user of the wireless communications system, the user may activate his badge and may receive a prompt indicating that the server is ready to handle the user's requests. The user may then say a voice command, such as "Call Rob Shostak", into the badge that records the voice command in digital form and communicates the digital data corresponding to the voice command to the server through the access point. The server may then interpret the voice command. Once the voice command is interpreted, the server may execute the appropriate function in order to set up a call between the badge user and the Rob. For example, the server may look up Rob in its user database to determine if Rob is a user of the system and has a badge. If Rob is a user, then the server will attempt to locate Rob and then set up a badge to badge call. When the call is established, audio is directed from the badge user, to the neighboring access point, then the network to the access point to which Rob's badge is currently associated, through to Rob's badge. The two access points may actually be the same, in which case the middle "leg" through the network backbone is obviated. If Rob is not a user of the system, then the server will establish a communications session with Rob using Rob's telephone number and then hand over the communications session to the badge. When the call is established between the badge user and Rob, the communications path is between the badge, through the access point, the server, and the PBX, to Rob.

Thus, in accordance with the invention, a wireless communications system is provided. The wireless communications system comprises a central computer, one or more wireless access points connected to the central computer by a computer network wherein each access point has a coverage area, and a badge that communicate using a wireless protocol with one of the wireless access points that the badge is within the coverage area of, the badge further comprising a microphone that receives voice commands and spoken words from a user and a speaker that generates audible signals heard by the user. The system permits a telephone call to be initiated by a voice command from the user into the microphone of the badge and the telephone call is carried out using the microphone and speaker of the badge.

In accordance with another aspect of the invention, a wireless communications unit for hands-free communication with a wireless communications system is provided. The unit comprises a central processing unit that controls the operations of the unit, a microphone connected to the central processing unit that receives voice commands and spoken words from a user and a speaker connected to the central processing unit that generates audible signals heard by the user. The unit further comprises a wireless transceiver connected to the central processing unit that communicates with the wireless communication system using a wireless protocol, and wherein a telephone call is initiated by a voice command from the user into the microphone of the unit and the telephone call is carried out using the microphone and speaker of the unit.

In accordance with yet another aspect of the invention, a method for locating a user of a wireless communications system wherein the wireless communications system has a central computer connected to one or more access points which communicate wirelessly with one or more badges associated with a user is provided. The method comprises receiving a request to locate a particular user of the wireless communications system, determining the access point currently being used for communications by the badge of the particular user, and generating a location indicator for the particular user wherein the location indicator is the name and location of the access point being used by the particular user.

BRIEF DESCRIPTION OF THE DRAWINGS

FIGS. 2a-2g illustrate a first embodiment of the communications badge in accordance with the invention;

FIG. 3a-3h illustrate a second embodiment of the communications badge in accordance with the invention;

FIGS. 3j-3y illustrate two preferred embodiments of the communications badge in accordance with the invention;

FIG. 11 illustrates an example of a preferred menu organization for the badge in accordance with the invention; and FIG. 12 illustrates an example of a menu state table showing the transitions between the various menus states.

DETAILED DESCRIPTION OF A PREFERRED EMBODIMENT

The invention is particularly applicable to a voice-controlled wireless communications system that uses Bluetooth or IEEE 802.11 as a communications protocol and a Ethernet communications/computer network and it is in this context that the invention will be described. It will be appreciated, however, that the voice-controlled wireless communications system in accordance with the invention has greater utility since it can be implemented using various different communication protocols and various different computer networks.

Figure 1:
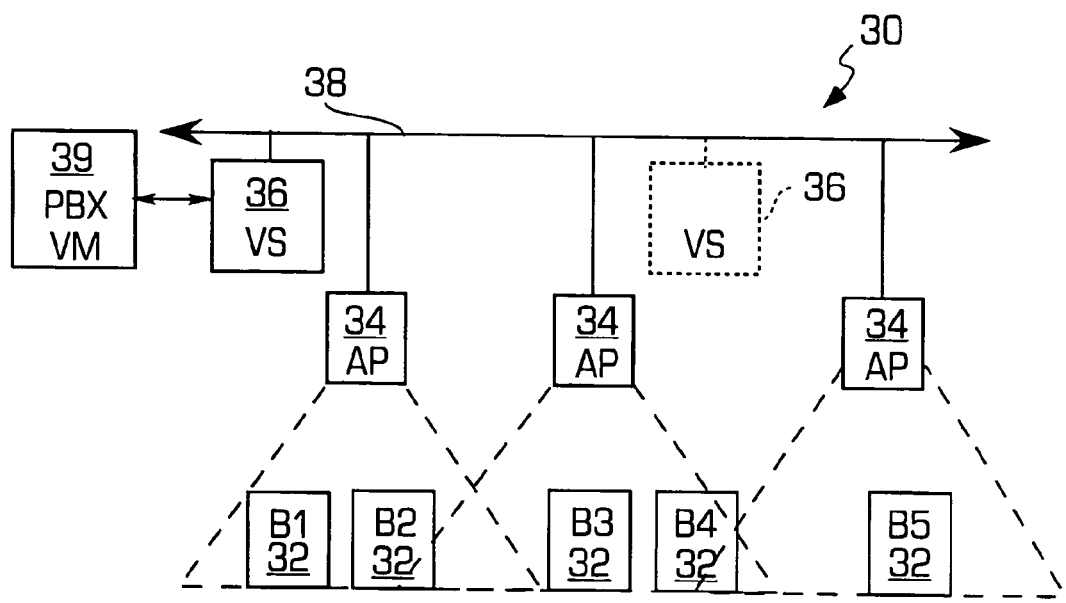
FIG. 1 illustrates an example of a preferred embodiment of the voice-controlled wireless communications system in accordance with the invention.

FIG. 1 illustrates an example of a preferred embodiment of the voice-controlled wireless communications system 30 in accordance with the invention. In particular, the system comprises a plurality of wireless user badges (B1-B6 in this example) 32, one or more wireless access points (AP) 34 and one or more central computers (VS) 36, such as a server computer, as shown. In this figure, a local area network wireless communications system is shown that permits communication between badges in the same building wherein the access points 34 and the server 36 are connected to each other and communicate with each other over a communications/computer network 38 which may be a local area Ethernet network. The voice-controlled wireless communications system, however, is not limited to being implemented using a LAN since it may also be implemented using any other type of computer network. For example, for a large company with multiple buildings, a company wide voice-controlled wireless communications system may be provided wherein the building may be interconnected using a wide area network (WAN), there may be a central computer 36 located at each building which communicates with other central computers over the WAN, and each building may have a LAN with a central computer 36, one or more access points 34 and a plurality of badges 32. In a preferred embodiment, the computer network may be an Ethernet based network, the central computer 36 may be a typical server computer with additional features described below, each access point 34 may be a wireless access point that uses a particular wireless protocol, such as Bluetooth or the IEEE 802.11 standard and the wireless badges 32 are capable of communicating with the access points using the particular protocol. Thus, if the access points are implemented using the Bluetooth protocol, then the badges will have Bluetooth transceivers or if the access points are implemented using the IEEE 802.11 standard, then the badges will have 802.11 compliant transceivers.

Returning to the system shown in FIG. 1, a voice-controlled wireless communications system is shown that has a primary central computer 36 and a backup central computer (shown in phantom) that are both connected to the computer network 38. Each central computer 36 may also be connected to a telephone system 39, such as the public branch exchange system (PBX) and voicemail (VM) system shown, that permits the server to set up, manage and take down communications sessions between a user of the system that has a badge and a third party. Each access point 34 is also connected to the computer network 38 and communicates with the central computers 36 over the computer network. The access points 34 each have a limited range of operation/coverage 40, known as a network neighborhood, as shown. To permit handoff between access points as a person with a badge moves between different network neighborhoods, the network neighborhoods may preferably overlap to permit handoff without dropping a communications session. The access points may communicate with each badge 32 using a wireless protocol, such as Bluetooth or the IEEE 802.11 standard. In general, each access point is capable of handling some maximum number of active badges (e.g., badges that are actively communicating with the central computer or actively engaged in a call with someone) so that more than one access point may be needed in a particular high density area with multiple badges. Each badge 32 is a small, lightweight, voice-controlled, wireless device that is capable of communicating with an access point. Each badge is preferably powered by a rechargeable battery. In general, each badge is an access device to the voice-controlled wireless communications system, but does not perform much of the actual processing (other than audio processing which may include voice compression and echo cancellation) since the processing power of each badge is relatively small. Thus, each badge will communicate with the central computer 36 through an adjacent access point in order to implement the desired wireless communication functions that are described in more detail below.

In operation, a user that wants to initiate a wireless communications function may activate his/her badge in some manner. The activation causes an adjacent access point (where the badge is within the network neighborhood of the access point) to establish a communications session with the particular badge. The user is notified that activation is complete and then speaks his command which is received by the badge using its microphone and converted into digital data. The based may then communicate the digital command data to the access point which in turn sends the digital command data to the central computer 36 over the computer network. The server may then analyze the digital command data in order to determine the command issued by the user, such as "Where is Paul Barsley". If the central computer is able to properly identify the command, then it will execute the appropriate instructions to perform the commanded operation. If the central computer cannot properly interpret the command, it may request the user to try the command again. In this manner, the user is able, using only his voice, to perform various wireless communication functions wherein the central computer implements most of the functions. Now, the badge 32 will be described in more detail.

Figure 3I:
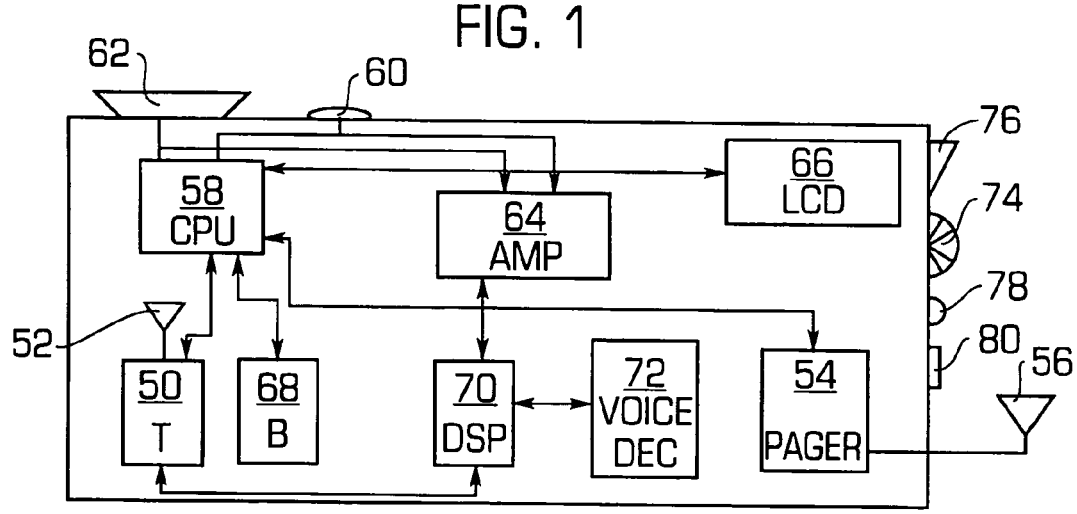
FIG. 3i is a block diagram illustrating the hardware components of the communications badge in accordance with the invention.

FIGS. 2a-2g illustrate a first embodiment of the communications badge 32 in accordance with the invention, FIG. 3a-3h illustrate a preferred embodiment of the communications badge in accordance with the invention and FIG. 3i is a block diagram illustrating the hardware components of the communications badge in accordance with the invention. Before describing the details of the badge or the different embodiments, a general overview of the badge and its operation will be provided. Each badge is a portable, battery-powered, lightweight, wireless device that serves as the primary communications endpoints of the system. The badges support hands-free, near full duplex voice communications using a small microphone (situated near the top of the badge as described below) and a speaker (located near the bottom of the badge as described below). In addition to the wireless communications, each badge is preferably capable of receiving text pages (using a pager receiver as described below) or from an e-mail client in the server 36 or from a browser application hosted on the server 36 and may include a display unit (as described below) to, among other things, permit reading of the text pages.

Each badge is only capable of voice communications when it is within the network neighborhood of any access point. The typical range of a wireless access point is approximately 35 meters for an indoor access point and approximately 100 meters for an outdoor access point. Thus, when the badge is not within the range of any access point, voice commands do not work. However, the badge may still be used as a one-way text pager anywhere within the coverage area of a global pager service network.

The badges are sufficiently small and lightweight enough so that the badge may be clipped onto a shirt pocket of the user, may be worn on a lanyard around the neck of a user or carried is a holster similar to cellular phone. In a typical environment with typical noise levels, hands-free operation using voice commands requires the badge to be situated approximately 0.5 meters from the mouth of the user so that the voice commands may be understood by the central computer. Thus, if the badge is carried in a holster, it may need to be removed from the holster and brought closer to the user's mouth for voice command, hands-free operation. For a semi-private conversation or operation in a loud environment with high noise levels, the badge may be inverted (so that the speaker is near the user's ear and the microphone is near the user's mouth) similar to atypical telephone. Optionally, a headphone jack may be provided on the badge. The badge may also include a clip (as described below) that may be used to clip the badge onto a shirt or shirt pocket or may be used to hold a corporate security badge.

The badges may be powered by a renewable energy source, such as a replaceable, rechargeable lithium polymer or lithium ion battery, that attaches to the back of the badge. The battery may be needed to be recharged each day for voice operation, but it may last longer if the badge is used for only text functions. The invention, however, is not limited to any particular energy source and any renewable energy source may be used. The badge may include a charging adapter as an accessory for recharging the renewable energy source and the charging adapter may be a docking station or simply a wall transformer.

Returning to FIG. 3i, a block diagram of the badge 32 is shown. Each badge may include a wireless transceiver 50 and an antennae 52 (that may be a 100 mw Bluetooth radio transceiver, an appropriate strength IEEE 802.11 transceiver or any other wireless transceiver) that is used for wireless communications with the access points 34 or with other badges as described below. In a preferred embodiment, each badge contains an 802.11b transceiver capable of transmitting at approximately 20 dBm (100 mW), and receiving with a sensitivity of approximately −85 dBm. The badges also contain a DSP engine and voice codec for speech processing and control, a display control processor and LCD display, a lithium battery with protection circuitry, an audio amplifier, microphone, and speaker. Each badge is factory-assigned a unique physical (MAC) address. Each badge may further include a pager receiver 54 and an internal antennae 56 (such as a Motorola FLEX pager receiver and antennae) that operates to receive text messages/pages within the coverage of any global paging service network. The antennae for the wireless transceiver, in a preferred embodiment, may be built into the clip of the badge or may reside completely within the badge. Each badge is assigned a unique wireless device address (so that it can be identified by each access point and the central computer) as well as a unique pager address, such as a FLEX pager CAP code.

Each badge may further include a central processing unit (CPU) 58 that controls the operation of the badge and each of its components including the wireless transceiver 50 and the pager receiver 54 as shown. For example, the CPU may also control a microphone 60 and a speaker 62 that are components of the badge and permit the user of the badge to communicate with the central computer 36 using voice commands and receive voice responses from the central computer 36. The badge may further include a well known non-volatile memory chip (not shown) so that data stored in the badge (such as settings and messages) are not lost when the badge is powered down. For example, the non-volatile memory device may be a well known flash memory device. The microphone and speaker may also be used for voice communications with other badge users or third parties. The badge may further include an amplifier 64 that amplifies the signals provided to/from the microphone and speaker.

The badge 32 may also include a display device 66, such as a liquid crystal display (LCD), that may be used for various purposes, such as reviewing text messages and pages received by the pager receiver, to permit the user to control the operation of the badge and its configuration using a control menu or to announce the origin of an incoming call. In a preferred embodiment, the display device 66 may be a monochrome dot-matrix display with approximately 32 rows and 60 columns. The display has sufficient resolution to permit four lines of approximately fourteen characters per line. In the preferred embodiment, the display device 66 may be situated on the back of the badge (as shown in FIG. 3c) to protect it from damage and so that it is not normally visible without flipping over the badge or removing it from its holster. As described above, the badge may include a renewable energy source 68, such as a removable, rechargeable batter as shown, that may include protection and charge management circuitry as is well known to prevent overcharging. The badge may further comprise a digital signal processor (DSP) 70 and an audio codec 72 for processing incoming speech from the microphone and for generating the voice signals generated by the speaker. For example, the DSP and audio codec are capable of compressing the digital voice data to reduce the amount of digital data used to communicate the voice commands to the server. The compression is performed by a commercially available compression software sold by VoiceAge.

The badge 32 may further include an input device 74 that permits the user to control the operation of the badge and its configuration. In one embodiment, the input device may be a jog switch which is a spring-loaded compound-action switch that supports three momentary actions. In particular, the switch may be pressed inwards as an ordinary push button. The switch may also be rotated in either direction. The function of these actions depends on the context. For example, if a call is in progress, the up and down movements may control volume. When a call is not in progress, these movements may control menu and message scrolling in the display. Certain input operations may require that the switch is pushed in for more than some predetermined amount of time. In the following descriptions, it will be convenient to speak of the jog control as if it were three separate buttons for clarity. Therefore, the inward push control will be called the activate button; the other two controls will be referred to as the scroll up and scroll down buttons. Many jog operations are carried out by pressing and releasing almost immediately; we will say "press the activate button", for example, to mean press and quickly release. A few operations require holding for some predetermined period of time, such as at least half a second, before releasing. We will say "press and hold" in this case. Thus, the user interacts with the system through a combination of the jog switch and voice controls. In a preferred embodiment, the input device 74 may be a touch button location in particular location, such as on the front of the badge, that may be pushed or touched to activate the same functions and operations being activated by the jog switch.

The badge may also include an on/off switch 76 and a status indicator 78. In a preferred embodiment, the status indicator may include an LED that is capable of displaying one or more different colors to signal the operational status of the badge. For example, a slowly blinking green light indicates that the badge is within the network neighborhood and is operational while a slowly blinking read light indicates that the badge is not within a network neighborhood. The badge may further optionally include a headset jack 80 that enables the user to plug in an external microphone/speaker headset, such as an ear bud. When the external headset is plugged into the jack 80, the operation of the internal microphone and speaker is inhibited.

The wireless system must know which badge each user is wearing so that calls to the user can be properly routed. Badge assignment is the process of associating a badge with a particular user. The assignment may occur when a badge is first activated. At that time, the system prompts the user to identify himself verbally. Depending on the installation, it may also be necessary for the user to say a password provided to him by the administrator, or a voice signature that is matched against a pre-recorded entry in the database of the server 36. Assuming the user is known to the system, the system will recognize the name, and will then (after a confirmation) assign the badge to the user. When the badge has been dynamically assigned to the user, the user's profile stored on the server 36 will be associated with the particular badge so that, for example, the user's preferences are active or the alternate names of the user are known. Once assigned, the serial number of the badge will show up on the user's console (as described in more detail below), and the badge can display a welcome greeting, when turned on, that is personalized to the user (e.g., "Hello, John"). The server 36 may also store text messages that may be downloaded to the badge at this time. A given badge can be assigned to at most one user at a time, and each user can be assigned only one badge at a time. A badge can later be reassigned to another user, if desired, via a voice command. Alternatively, the system administrator can explicitly set the serial number of the badge to be assigned to a user through the user console. In accordance with the invention, a badge is not tightly bound to a single user as would be the case with a cellular phone, wireless e-mail device or other devices. In accordance with the invention, the badge is dynamically bound to the user when the user uses the badge. As an example, when a badge is not being used by any particular user, it is not assigned to any user and is available for use by any user. When the user is assigned to a badge, the user profile on the server is associated with the badge. However, the user profile is not stored on the badge since the badge is merely a device used to access the system. As an example, a company may have 50 badges which are available for use. In accordance with the invention, when a user needs a badge, such as at the start of a workday, the user is assigned a badge (as described below) and uses the badge. At the end of the day, the user returns the badge to the charger station and the badge returns to an unassigned state in which any user may pick up and be assigned to the badge.

The bearer of the badge must typically first be registered with the system (or be registered by the administrator) before the badge can be assigned to him. In cases where visitors may be provided with a badge to be used temporarily, it may be useful for the administrator to register a few "Guest" users (the registration process only takes a moment) and assign guest badges to them. If desired, the spoken name of the guest can be entered through the user console, so that other users can hail him by name as opposed to, say, "Guest Three". As noted above, the assignment process entails that the user speak his own name so that he may be recognized by the system. The name will be recorded by the system and used for constructing a confirmation prompt when other parties call ("Finding . . . John Smith"). If the spoken name of the user is later changed in the User Console, the user will be prompted to re-speak the name the next time his badge is successfully activated. The user is similarly prompted to speak the identifying phrase ("John Smith in Sales") if one is provided.

Returning to FIGS. 2*a*-2*g* and 3*a*-3*h*, two different embodiments of the badge 32 in accordance with the invention are shown wherein the preferred embodiment of the badge 32 is shown in FIGS. 3*a*-3*h*. In the embodiment shown in FIGS. 2*a*-2*g*, the badge does not include a display device whereas the preferred embodiment shown in FIGS. 3*a*-3*h* includes the display device 66. Both of the embodiments of the badge include a clip 82, a microphone opening 84 and a speaker opening 86. Each embodiment also includes the input device 74, the on/off switch 76, the status indicator 78 and the headset jack 80 as shown. In the two embodiments shown, the status indicators 78 may be a series of LED lights. As shown in these two embodiments, the exact location of the various components on the badge may be varies without departing from the scope of the invention.

FIGS. 3*j*-3*y* illustrate two preferred embodiments of the communications badge 32 in accordance with the invention. These embodiments of the badge have the same elements as the prior embodiments so those elements will not be described. The embodiment shown in FIGS. 3*j*-3*q* has the clip 82 as shown while the embodiment shown in FIGS. 3*r*-3*y* does not have the clip. Both of these embodiments do not include the jog switch, but have a different device. In the preferred embodiments shown, the display 66 may be a monochrome dot matrix with a grid size of 32 rows by 60 columns. The grid is sufficient to display up to four lines of approximately 14 text characters per line in a 5-point font. The display is situated at the back of the badge, and so is normally not viewable without some manipulation from its normal position. The display is used to indicate badge status (such as battery charge, on-off network status, and signal strength), to peruse text messages, to announce the origin of incoming calls, and for various control menu functions. In addition to the elements of the other badges, these badges include a activate button 87 and a do not disturb/hold button 88.

The activate button 87 is the primary control with which the user interacts with the badge and is a momentary push button on the front of the badge as shown. This button is used to initiate a dialog with the system agent (the "Genie"), as well as for various call control functions. The activate button supports two momentary actions; it may either be pressed and immediately released (a press), or pressed and held down (a press-and-hold) for longer than a brief moment. The length of a "brief moment" will need to be determined through experiment, but is likely to be approximately 600 milliseconds. While the functions of press and press-and-hold depend on the context, the general rule is that a press is used for an affirmative action (such as initiating or accepting a call). The press-and-hold is used to power down the badge.

The do not disturb/hold button 88 is a second momentary push button that is provided at the top of the unit as shown to allow the user to place the badge in a do-not-disturb (DND) mode (if no call is currently in progress), or to put a call on hold (if one is in progress). The button acts as a simple toggle. This button is backlighted by a single-color LED that is normally inactive, but turns on when in DND or Hold mode. It may be useful to distinguish between the two modes by having the LED blink while in DND mode, and continuously illuminated while a call is on hold, for example.

The input device 74 in these embodiments is a group of three small momentary push buttons is situated along one edge of the badge to facilitate volume adjustment during calls, and manipulation of the display menus when no call is in progress. The top and bottom buttons of the group increase and decrease call loudness, respectively, when a call is in progress. When the badge is inactive, they act as scroll controls for manipulating menus and text on the display. The middle button is used to make menu selections in this context.

The status indicator 78 in these embodiments is an LED display which is capable of displaying two colors is used to signal operational status. For example, a fast blinking green indicates that a message is waiting. Other blinking patterns (such as blinking red) may be used to indicate other conditions, such as hand-off in progress or low battery. The headset jack 80 is provided to enable one to plug in an external microphone/earphone combination. Use of the jack inhibits the operation of the built-in microphone and/or speaker. Now, the wireless access points in accordance with the invention will be described in more detail.

Figure 4:
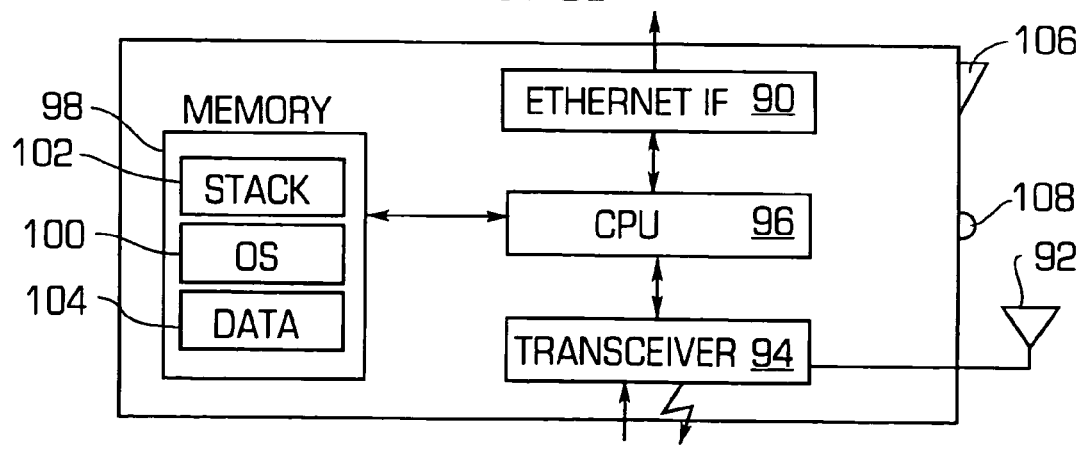
FIG. 4 is a block diagram of an exemplary access point in accordance with the invention.

FIG. 4 is a block diagram of an exemplary access point 34 in accordance with the invention. As described above, the wireless system 30 may include at least one and typically several access point units situated at various locations within the customer premises so that the network neighborhoods of the access points preferably overlap. Each access point 34 is connected to the computer network 38 as shown in FIG. 1 by a computer network interface 90. Depending on the installation, the access point may be plugged into as standard RJ45 Ethernet jack (intended typically for workstation nodes) using the Ethernet interface as shown in FIG. 4 and it may be mounted on the wall. Alternatively, the access point may be located within the area above a drop-down tiled ceiling. The power for the access point may be provided by the network cable itself (according to a new standard) or the access point may be connected to a AC source.

Each access point may include an external antennae 92 which may be supplied in several different variations, depending on the requirements of the particular installation. For example, the antenna may have directional gain and may be mounted outside the building and connected to the access point via a feed-through through a window for an outside access point. Alternatively, the antennae may be mounted adjacent to the access point inside of a building area.

In principle, each access point serves a predetermined radius. The actual radius depends on the type of wireless technology being used. For example, for a Bluetooth wireless technology or 802.11 wireless LAN, a radius of approximately 35 meters of coverage indoors and 100 meters out-of-doors may be typical. Each such area of coverage is said to be a cell. As described above, access point spacing must be such that there is sufficient cell overlap that hand-off of badges from one access point to the next can be accommodated. The spacing of access points is also a function of the anticipated conversation density. In particular, each access point is typically able to manage up to seven active badges (i.e., seven concurrent active connections). In situations where a greater number of active connections are likely within a given area, cell size can be reduced (and the number of access points increased).

Each access point further comprises a wireless transceiver 94 connected to the antennae that communicates with the badges. In one embodiment, the transceiver may be a Bluetooth transceiver while in a preferred embodiment, the transceiver may be a radio transceiver that implements the IEEE 802.11 standard. The access point may further include a central processing unit (CPU) 96 that controls the transceiver and the computer network interface 90. In a preferred embodiment, the CPU may be a 32-bit RISC processor. The access point may further include memory 98 (which may include both memory chip devices as well as persistent storage devices) that stores the instructions and software used by the CPU 96 to control the operation of the access point. For example, the memory may include an operating system 100, an Ethernet-based TCP/IP stack 102 and data 104 associated with the operation of the access point. For example, the access point may temporarily buffer the voice data from a badge prior to communicating it to the central computer over the computer network. The access point may also include a control switch 106, such as an on/off switch and a status indicator 108, such as a pilot LED.

Figure 5:
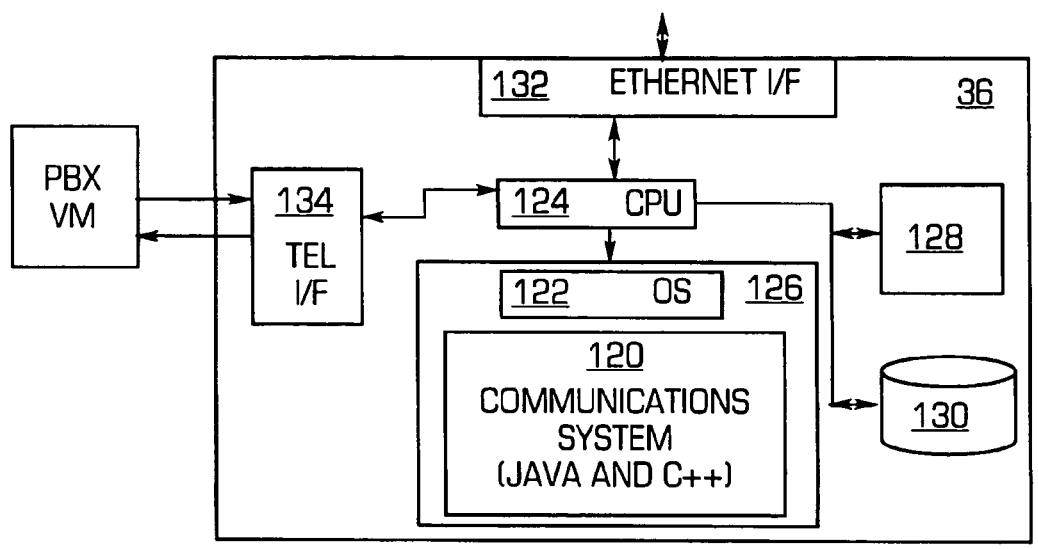
FIG. 5 is a block diagram of an exemplary server in accordance with the invention.

As is well known, each access point is factory-assigned a unique network medium access control (MAC) address and can be assigned an IP address either through a dynamic host configuration protocol (DHCP) or through wireless programming using special wireless communication system installation tools (e.g., possibly a badge with special firmware). Now, the central computer (a server in the preferred embodiment) will be described in more detail FIG. 5 is a block diagram of an exemplary server 36 in accordance with the invention. The server 36 is responsible for the overall control of the system. The server consists of a set of Java and C++ application programs 120 running on an Windows-based operating system 122 on Windows NT or Windows 2000 platforms, together with special-purpose hardware needed for telephony integration. In more detail, the server 36 may include a central processing unit (CPU) 124 and a memory 126 that stores software currently being executed by the CPU such as the operating system 122 and the JAVA and C++ applications 120 that implement the wireless communication functions of the wireless communications system. The server further comprises a persistent storage device 128, such as a hard disk drive, an optical drive, a flash memory or the like and a database 130 that stores information associated with the wireless communications system. The database stores user information, including the assignment of users to badges, speech files containing user name prompts and voice signatures, user preferences, buddy lists, text messages and voice messages. It also keeps track of the whereabouts of users as they roam within the communications network. In large corporate installations, this component may interface to global employee databases maintained by the customer. The database may also reside on a computer that is physically separate from the main server 36 and may be replicated for fault-tolerance. A standard commercially-available database such as those based on SQL may be used.

The server 36 may further include a computer network interface 132, such as the Ethernet Interface shown, that permits the server to be connected to the computer network and a telephone network interface 134 that permits the server to be integrated with a typical telephone system that may include, for example, a public exchange telephone system and a voicemail system. The server typically resides in the same location as the customer's telephone equipment so that it can interface to the PBX and the voicemail system. The telephony gateway component of the server 36 could also reside in a separate computer that communicates to the server 36 through the network.

Figure 6:
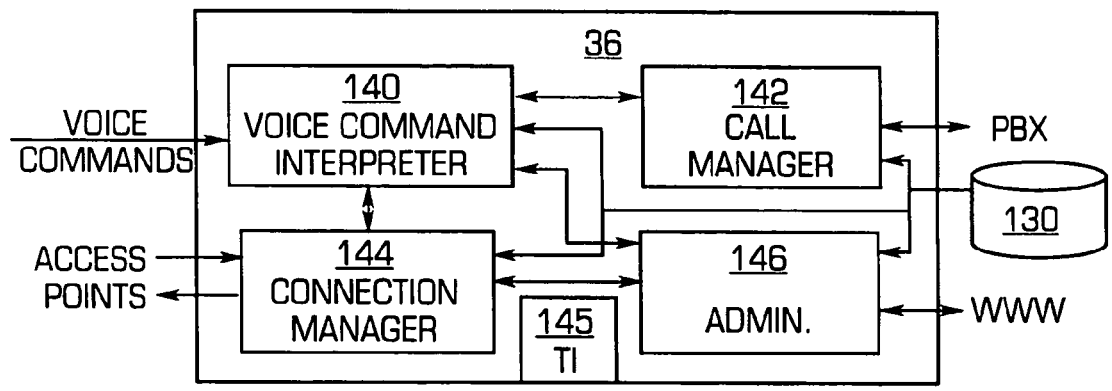
FIG. 6 illustrates more details of the server shown in FIG. 5.

FIG. 6 illustrates more details of the server 36 shown in FIG. 5. In particular, the functional blocks of the software 120 and the database 130 are shown in more detail. The software may include a voice command interpreter 140, a call manager 142, a connection manager 144 and an administrator 146. The voice command interpreter 140 may be a component that includes a speech engine, such as the commercially available Nuance speech engine, is built onto the speech engine and has responsibility for interpreting and executing voice-based commands from both badges and externally initiated calls coming in from the public switched telephone network (PSTN). The call manager 142 has responsibility for the set-up and the breakdown of two-party and multi-party calls and maintaining status information associated with these calls and its connection to the PSTN or PBX as is well known. The connection manager 144 is the component that is responsible for managing access points and the connections between badges and access points and among the badges. It supports hand-off from one access point to another (or one subnet to another) as a badge roams about the network and it informs the badges of the IP addresses of the other badges with which they are to communicate. The connecting manager also supports roaming across different sub-nets. In particular, when it is determined that a badge has crossed a sub-net boundary (since the connection to the badge has been lost), the badge will request a new DHCP address and then communicate that new information to the server 36. The server 36 may then communicate the new address to the other badges in the system so that, for example, a conversation may be continued following the roaming of the badge in the network.

The administrator/user module 146 (a browser application manager) supports administrator-level and user-level configuration and monitoring of the system through a web browser interface as shown. A telephony integration component 145 may include hardware and software needed for the system to interoperate with the phone network. The hardware typically consists of one or more Dialogic or similar cards, such as a Dialogic D/120JCT-LS card which has twelve analog ports, installed within the server machine, which might interface to a T1 trunk at the company PBX. The card is connected to the customer's telephone system via standard cables. The twelve ports enable twelve simultaneous connections to PBX extensions or outside numbers. The software will support an IVR interface that permits calls originating from the outside to be routed to the appropriate user.

The database 130 stores user information, including the assignment of badges to users, speech files containing user name prompts, messages, user preferences, buddy lists, text message and voice messages. It also keeps track of the whereabouts of users as they roam within the communications network, as well as the MAC address of each badge and the IP address currently assigned to each badge. Once a user has logged into the system (and has a badge assigned to him), the database record for that particular user may be cached into the memory of the server using a hash table so that the user information may be more readily accessed. In large corporate installations, this component may interface to global employee databases maintained by the customer. The server 36 may also contain a web server, such as an Apache server, that hosts the user/administration console.

Figure 6A:
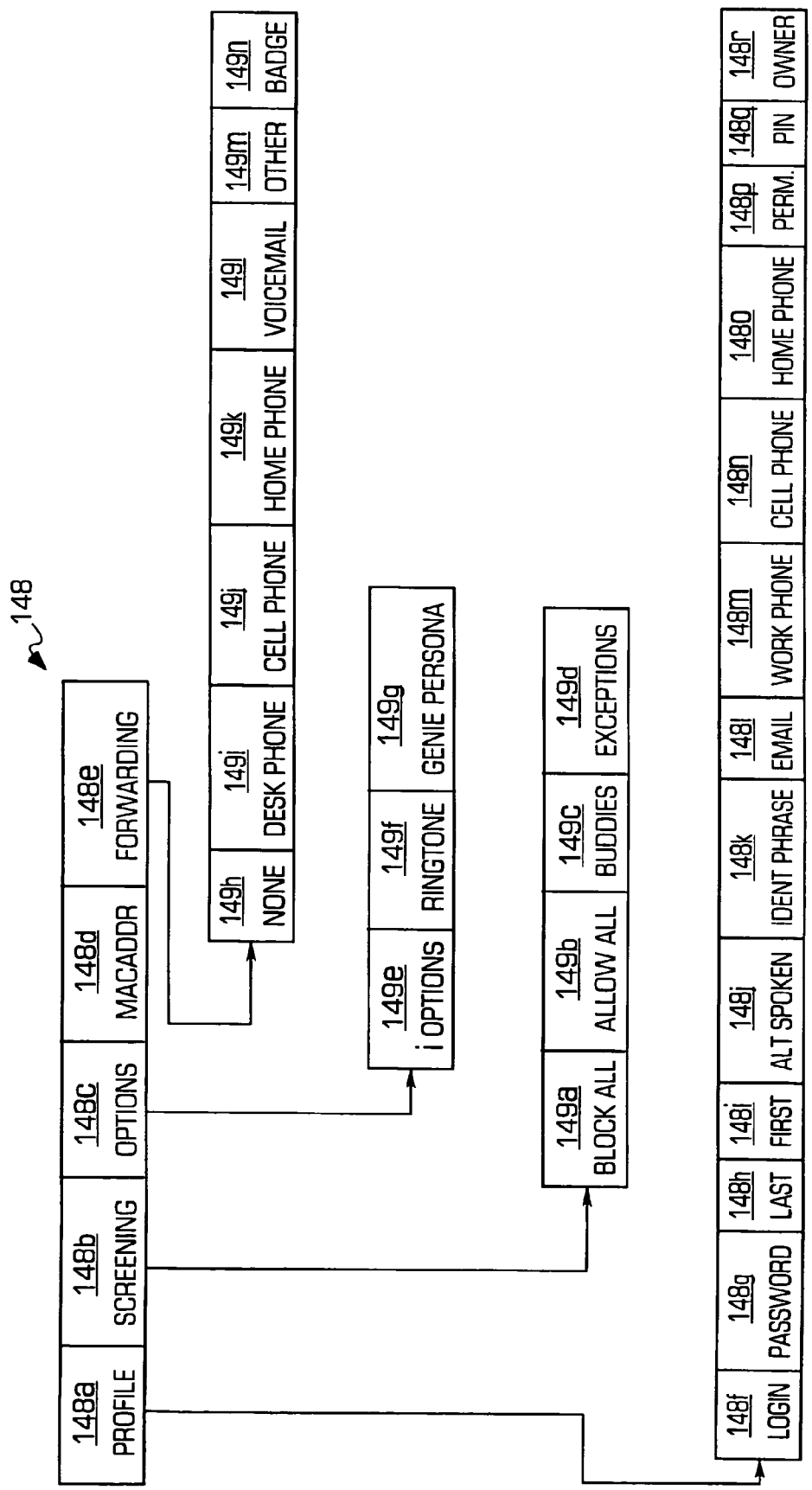
FIG. 6A illustrates an example of the user database in accordance with the invention.

FIG. 6A illustrates an example of a portion of the user profile database record 148 in accordance with the invention. This example does not include every element of the user profile database, but is merely illustrative. A complete listing of the user profile database is provided in the attached appendix A. As shown in FIG. 6A, the user profile database record may comprise a profile portion 148a, a screening portion 148b, an options portion 148c, an address portion 148d and a forwarding portion 148e. The profile portion 148a contains various information about the particular user of the system as will be described below in more detail. The screening portion 148b contains information about how calls coming into the badge will be handled for the particular user. The options portion 148c contains information about various system options and address portion 148d may contain information about a MAC address for the badge which is currently assigned to the user and an IP address. The forwarding portion 148e contains information about how calls going to the badge for the user are forwarded when the user is not available.

In more detail, the profile portion 148a comprises a login field 148f containing login information about the particular user, a password field 148g which contains the password of the particular user, a last field 148h containing the last name of the particular user, a first field 148i containing the first name of the particular user, an alternative spoken name field 148j that contains other spoken names for the particular user, an identification phrase field 148k which contains a phrase used to identify the particular user, an email field 148l containing the e-mail address of the particular user, a work phone field 148m containing the work phone number of the particular user, a cell phone field 148n containing the cell phone number of the particular user, a home phone field 148o containing the home phone number of the particular user, a permissions field 148p containing the permissions which the particular user has, a PIN field 148q containing the PIN number of the particular user and an owner field 148r containing the owner name. The screening portion 148b may further comprise a block all field 149a containing a flag which indicates that the user is currently blocking all calls to the badge, an allow all field 149b containing a flag indicating whether the user is currently allowing all calls to his currently assigned badge, a buddies field 149c containing the buddies for the particular user and an exceptions field 149d containing the exceptions for the block all and allow all options.

The options portion 148c may further comprise an iOptions field 149e containing the options for the user, a ringtone field 149f containing the ringtone selected by the user at the particular time and a Genie persona field 149g containing the particular Genie persona currently selected by the user. The forwarding portion 148e may further comprise a none field 149h containing a flag that no call forwarding is currently in place, a desk phone forward field 149i containing a flag indicating that call may be forwarded to the user's desk phone, a cell phone forwarding field 149j containing a flag indicating that call may be forwarded to the user's cell phone, a home phone forwarding field 149k containing a flag indicating that call may be forwarded to the user's home phone, a voicemail field 149l containing a flat indicating the a call may be forwarded to the user's voicemail, an other field 149m containing a flag indicating that the call may be forwarded to another destination, and a badge field 149n containing a flag indication that the call may be forwarded to another badge. Now, the user console will be described in more detail.

Figure 7:
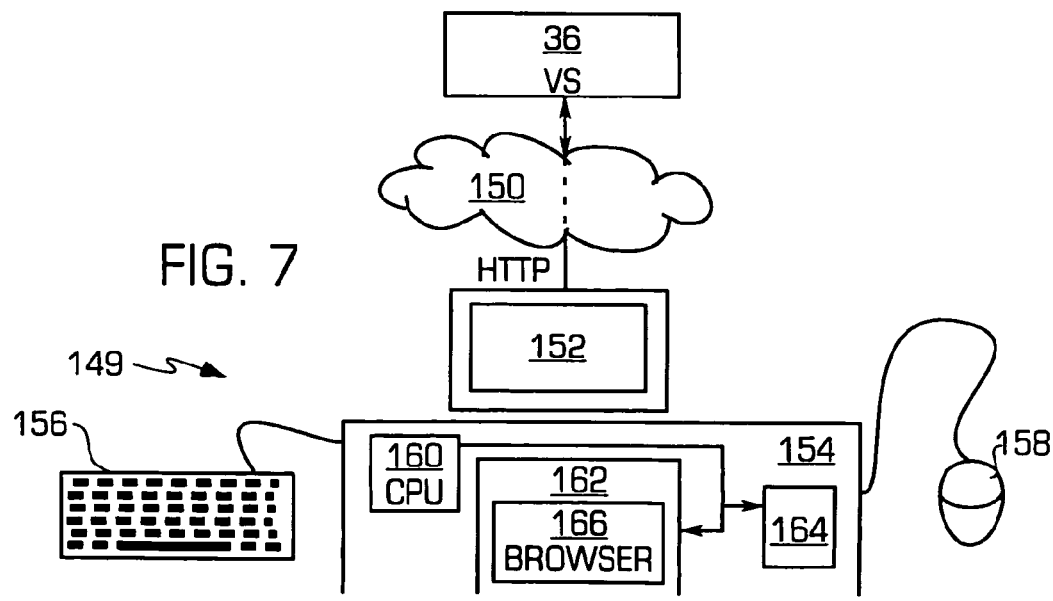
FIG. 7 illustrates an example of a user/administrator console in accordance with the invention.

FIG. 7 illustrates an example of a user/administrator console in accordance with the invention. In particular, the user console in accordance with the invention may be implemented when a computer 149, such as a personal computer, is used to access the server 36 over a computer network 150, such as the World Wide Web, that uses the typical HTTP protocol. The computer 149 may include a display unit 152, a chassis 154 and one or more input/output devices, such as a keyboard 156 and a mouse 158. In more detail, the chassis may include a central processing unit (CPU) 160, a memory 162 that stores software currently being executed by the CPU and a persistent storage device 164, such as a hard disk drive. To implement the user console functionality, a typical browser application 166 may be downloaded into the memory and executed by the CPU. The browser will permit the computer to establish a connection over a communications link, such as a DSL modem line or the like, to the server 36 using the HTTP protocol. To permit the user to view the system information, the server may generate one or more web pages that are displayed on the display unit of the computer and the user may interact with the web pages to change the information of the system.

The user/administrator console is a browser-accessible web application through which users are registered with the system, and through which various profile information fields, preferences, group memberships and buddy lists can be set up. The application is hosted, in a preferred embodiment, using an Apache-based web server that is co-resident with the server 36. The application is accessible from anywhere within the customer's firewall via a login name and password. If desired, a customer could permit external access to the application so that a support person or some other agent could monitor and/or troubleshoot the system externally. The console also allows a user to retrieve saved text and voice messages and to view a call activity log.

Depending on a system administration option, new users can be allowed to self-register through the console, or may be registered via a batch entry process available only to the system administrator. In some environments (such as retail stores), the application may not be accessible to ordinary users at all. In such cases, the system administrator will be responsible for configuring all global and user-level settings. It is expected that various vertical markets will require both cosmetic and functional variations of the browser application. For example, in a corporate setting, all users can be safely assumed to have an e-mail address that can serve as a login ID. In a hotel environment, on the other hand, this may not be the case. Moreover, certain product features, such as choices of Genie personae and sound prompts, may need to be customized according to the vertical. Because the requirements for the various targeted verticals are still undetermined, not all of the following feature descriptions are expected to apply to every situation. The application may be entered via a login page that invites existing users to enter a login name and password, and new users to register themselves with the system (if self-registration is enabled).

The body of the application is organized-as a collection of web pages, each of which presents a set of related text fields, choices and interactions. The different pages are accessed via a columnar arrangement of menu buttons arranged at the left side of each page. Each field or control appearing on a page is accompanied by a brief title or comment explaining its function. In the case of the more subtle items, an information dot is provided that a user can click on to see a more detailed explanation. At the bottom of each page is a Save button that is ordinarily grayed out, but which becomes active when a user makes a change to the page. The button must be pressed to save any changes made to the page since the last save. As a safety provision, if the user navigates to a new page before saving, a dialog box is presented asking him whether or not he wishes to abandon his changes. In a preferred embodiment, the console may include a plurality of different user pages, including but not limited to, a basic information page, an announcement options page, a call screening options page, a buddy list page, a forwarding options page, a groups page and a miscellaneous options page.

In a preferred embodiment, the console may also include a plurality of administrator pages including but not limited to a systems option page, a user administration page, a badge status monitor page, an access point location page and a telephony options page. In typical customer environments, one (or more) of the users will be designated as system administrator, and will have responsibility for configuration and monitoring of the system. Because it cannot be assumed that the system administrator will have a technical background in every instance, nor have much free time to administer the system, it is a design goal that the administration mechanisms be as easy to understand and use as the rest of the system. System administration is effected through the browser application. When a user successfully logs in using the "Administrator" login ID, the usual pages of the application-are replaced by special pages that pertain exclusively to administrative functions. Beyond having access to the administrator pages, an administrator has the ability to put himself in the "shoes" of an arbitrary user. To do so, he simply logs in as the user in question, but supplies the administrator password. The information fields and various other settings and features that are accessible through the console will now be described. First, the administrator pages will be described and then the user pages will be described in more detail.

The system options page for the administrator contains fields and controls for managing system-wide preferences and policies. Below is a representative examples of the information on this page since the page may be augmented as more knowledge is gained about what needs to be included in this page. The page may include an administrator password field which is a text field that is initially blank at the time of installation, but should be filled in the first time the administrator logs in. The page may include a company name field which is text field containing the name of the company in which the system is installed. The page may also include a license key field which is a text field that gives the license key defining the number of users to which the customer is entitled. The page may include a self-registration option checkbox field which, when enabled, allows users to self-register through the browser application. If disabled, all users must be created by the administrator via the User Administration page detailed below.

The system options page may further include a default user permissions area which may include a series of checkboxes that allow the system administrator to specify a default set of capabilities that are enabled for all users. The permissions that are not checked off here can still be accorded to particular users from the User Administration page. The permissions include the following:

Location—which enables the use of "Where is?" and "Locate" voice commands.

Group Management—which enables display of the Groups page in the user browser application, which permits creation, editing, and deletion of groups. This permission also enables use of all group voice commands, including the Record Group Prompts voice command.

Group Add/Remove—which enables the "Add me to group" and "Remove me from group" voice commands.

VIP Status—which enables a user to complete a call to someone when he would otherwise be blocked. (In this case, the Genie first asks whether the call is urgent.) Note that users can give particular buddies this ability as well (see Buddy List page in the User Application.)

Ability to place internal calls through the PBX.

Ability to place external calls through the PBX.

Dynamic Badge Assignment—which enables the Log In and Log Out commands, which allow users to assign a badge to themselves at the beginning of a shift; and System Administration Voice Commands—which enables the Begin Tour, End Tour, Assign Location, and Record Location Prompt voice commands, allowing a user to administrate access point locations (see Access Point Locations page below).

The systems option page may also include a message sweep time area. As described in a later section, users of the system need not explicitly delete voice or text messages they have received. Instead, messages that are sufficiently old are automatically deleted. The message sweep time option determines how long old messages persist before they are deleted. This option is controlled by a drop-down box that enumerates choices of sweep times, ranging from several hours to several weeks. Another control is provided that defines the time of day at which the sweep occurs. The systems option page may also include an auto-logout checkbox field which, when checked, causes the system to automatically deassign (log out) and power off a badge when the badge is placed in a battery charger. This feature is useful in environments in which badges are shared among users. In such an environment, a user will typically take a badge from the gang charger at the beginning of a shift, and restore it to the charger at the end of the shift.

The administrator application may also include the user administration page. In many customer settings, the process of registering new users will be the responsibility of the system administrator, as opposed to the individual users themselves. Even in situations where self-registration is supported, the administrator may need to add new users to the system from time to time, and to remove users whose services are "no longer required". For these purposes, a User Administration page is provided that allows one to see the current set of registered users, as well as to add or remove users easily. This page also gives the administrator the ability to define permissions allowing particular users to engage in restricted activities. In an environment supporting telephony integration, for example, only certain users may be permitted to place outside calls.

The primary control on the page is a table listing the full name of each registered user. Clicking on a particular user in the table causes detail fields and controls for that user to be displayed on the page. These include the user's log in name, as well as all the permission checkboxes listed for the System Options page. Buttons are also provided for deleting the currently selected user, and for adding new user(s). This latter button brings up a cleared dialog box that displays the Basic Information fields. Pressing a Save button after filling out the dialog causes the newly-defined user to be added, and the dialog to be cleared to permit the entry of another user. Pressing a Cancel button in the dialog terminates the interaction, and dismisses the dialog.

The administrator application may also include the badge status monitor page which gives a real-time picture of the status of all badges that are currently within the network neighborhood. The display is in the form of a table with a row for each badge. The columns of the display provide the following information:

Full name of the user to which the badge is currently assigned (if any)

IP address

Note that IP addresses are assigned dynamically through the customer's DHCP server. Because the wireless LAN may encompass more than one subnet, the IP address of any given user can change as he roams about the premises.

Location

The user's location is actually the name of the access point with which the badge is currently associated. Access Point names are assigned on the Access Point Location Page described in the next section.

Call Status

This field shows whether and with whom (including the Genie) the badge is currently conversing.

DND/Hold Status

Miscellaneous

For testing/debugging purposes, it may be convenient to display other status information such as battery condition, signal strength, BER, and other hardware-related parameters. The page may also show aggregate statistical data that may be useful, such as the total number of active users, system up-time, average length of call, and so on. It may also keep track of metrics needed to monitor speech recognition engine usage for licensing purposes.

The administrator pages may include the access point locations page. The system provides a number of voice commands that allow users to be located within the network neighborhood. These commands depend on the definition of locations within the network. Locations may be chosen to designate buildings ("Building C") floors within buildings ("First Floor, Building C") or functional areas ("cardiology", "the cafeteria"). Each location is defined by one or more access points. Each access point, on the other hand, can be associated with at most one location.

In defining locations, one must bear in mind that radio propagation is a mercurial phenomenon, and that there is no guarantee that a badge will associate with the access point that is physically closest. Indeed, it is quite possible (though not very likely) for a badge to associate with an access point situated on a different floor. For this reason, location of users is an approximate business, which suggests that a courser location grid may be more useful than a finer one. In a campus environment, it may be sufficient simply to use building names. Doing so makes the location naming scheme easy to understand, and makes the location commands quite reliable. The Access Point Location page allows the administrator to define the set of locations, and to assign access points to each location.

The principle control on the page is a Locations list box enumerating the names of the various locations. Buttons are included to add a new location to the list, or to delete the currently-selected location. Selecting a particular location populates detail fields giving the following information:

Name Field

This text field gives the location name (such as First Floor) that appears in the Locations list box.

Spoken Name Field

This text field permits a phonetic pronunciation to be entered for the location. If none is provided, the value of the name field is used.

Description Field

This text field allows a more complete description of the location or comments to be entered.

In addition to the location list box, the page sports two detail tables. One of these (entitled Access Points) lists the MAC addresses of the access points assigned to the currently-selected location. Buttons are provided to add or remove an access point from the table. The second detail table, labeled Neighbors, lists locations that are adjacent to the currently-selected location. For example, the Cafeteria may be listed as a neighbor of Intensive Care. Defining neighbors allows the Locate voice command (described below) to be more useful, especially given the uncertainty of access point association noted earlier. Again, controls are provided for adding or removing a location from the neighbors list.

Because entering the MAC address of the access points for each location may be a tedious, time-consuming, and error-prone business (especially in installations having dozens or even hundreds of access points), a mechanism is provided to automate the process. The administrator first defines the location names by adding them to the Locations list box—this will usually take only a minute or two. The association of access points to locations is then made by taking a walking tour through the premises. The administrator begins the tour by issuing the Begin Tour voice command. As he roams around the premises, the Genie will announce each transition from one access point to another. At each transition, the Genie recites the MAC address of the access point, as well as the name of the location, if any, to which the access point is currently assigned. If no location is assigned, the administrator is invited to speak the name of the location to which the access point belongs. The MAC address of that access point is then automatically added to the list corresponding to the given location. The administrator invokes the End Tour voice command to terminate the session. As an additional aid, the Assign Location voice command is provided, which allows the currently associated access point to be assigned to a location at any time (whether touring or not). Note also that the MAC address and location of the currently associated access point can always be determined through the Info menu selection on the badge.

A Record Location Prompt voice command is also provided that allows a prompt to be recorded for a particular location. The prompt is used by system in conjunction with voice commands that utter location names. If no prompt is recorded, text-to-speech synthesis is used instead. The Begin/End Tour, Assign Location, and Record Location Prompt voice commands all require the user to have the system administration voice command permission. Three voice commands are provided to users that make use of locations. The "Where Is?" command permits location of a particular user. The "Locate" command allows one to identify members of a group who are currently in or close to a given location. For example, the command, "Locate technical support reps in the Cafeteria" would cause the Genie to find reps in the Cafeteria and neighboring locations. Finally, the "Where am I?" voice command allows one to identify the location of the access point with which he is currently associated. All of these commands require the user to be enabled for location.

The administrator application may also include the telephony options page. For installations in which telephony integration is implemented, the system will need to be configured so as to interoperate with the customer's PBX or voice mail system. Among the items that likely need to be specified are the following:

Telephony Installed

This check box field indicates whether or not telephony options have been installed.

Outside Access Enabled

This check box field controls whether users have the ability to place outside calls by default. If not checked, particular users can be granted this ability through the User Administration Page.

Outside Line Access Code

This text field defines the pattern of digits needed to obtain an outside line through the PBX.

Voice Mail Access Code

This text field defines the pattern of digits needed for direct access of the voice mail system through the PBX. Now, the various user pages will be described in more detail. The user pages include the basic information page. The basic information page contains fields giving background information for the user, including his name, phone numbers, e-mail address, and so on. This is the page at which a new user arrives from the login page, and is the only one containing fields that must be filled out in order to register. In the listing below, the required fields are notated with asterisks. Now, the user pages that are part of the application will be described in more detail.

As described above, in a preferred embodiment, the console may include a plurality of different user pages, including but not limited to, a basic information page, an announcement options page, a call screening options page, a buddy list page, a forwarding options page, a groups page and a miscellaneous options page. Each of these pages will now be described in more detail.

The basic information page contains fields giving background information for the user, including his name, phone numbers, e-mail address, and so on. This is the page at which a new user arrives from the login page, and is the only one containing fields that must be filled out in order to register. In the listing below, the required fields are notated with asterisks.

Login Name(*)

This is the unique identifier the user enters to gain access to the console/application. For example, "JSmith". In a corporate setting, it is likely to be the user's e-mail address. In this case, the e-mail address field (below) does the job, and no separate Login Name field is necessary.

Login Password(*)

Password may be used to gain access to the console (passwords may or may not be mandatory, depending on the system configuration). The system administrator password will always work as well.

First and Last Name(*)

Includes fields for first name and last name.

E-Mail Address

Gives the e-mail address to which voice messages are directed using the Send E-Mail voice command.

Desk Telephone No.

This is the user's desk phone number to which incoming calls can be redirected (see Unanswered Call Options below).

Cell Phone No.

This is the user's cell phone number, to which incoming calls can be redirected (see Unanswered Call Options below).

Home Phone No.

Spoken Name

This is the full spoken name other users should say to refer to this user. For example, "Call John Smith". The system retains, as part of the user's profile, a voice audio file that records the user's spoken name in that user's own voice. This audio file is used to construct a confirmation prompt when some other party calls the user. The file is recorded as part of the badge registration process described in a later section. The system will, by default, recognize the full name (first and last) of a user. Often, however, a user may go by a variation of his formal name—he may go by "Jim Smith", for example, rather than "James Smith". The spoken name field allows such a variation to be specified.

The spoken name field is also useful for providing a phonetically spelled variant in the case of a foreign name or a name with an unusual pronunciation. For example, Jim Beaumont might be given the spoken name, "Jim Bowmont". An information dot will be furnished to give the user some guidance as to how to develop a phonetic spelling. A phonetic pronunciation wizard may be provided as well.

The system retains, as part of the user's profile, a voice audio file that records the spoken name in a user's own voice. This audio file is used to construct a confirmation prompt when some other party calls the user. The Record Name voice command allows a user to record or re-record his name prompt. If no prompt has been recorded, the system synthesizes the name using text-to-speech.

Alternate Spoken Names

In many cases, a person may go by more than one name, or his name may be pronounced by different people in different ways. To provide for this eventuality, up to three alternative names may be supplied in addition to the primary spoken name. For example, "Kathy Johnson" might be a supplied as the primary name, while "Kate Johnson", "Katie Johnson", and "Miss Johnson" might be provided as secondary names. These alternate names are stored in the database 130 similar to the other user profile information.

Identifying Phrase

The identifying phrase is used to distinguish two users who may happen to have identical first and last names, such as John Smith. In such a case, their identifying phrases might be "John Smith in Marketing", and "John Smith in Sales", respectively. If a caller asks for John Smith, the Genie retorts, "Say either John Smith in Marketing or John Smith in Sales". If an identifying phrase is given, the Record Name voice command will prompt the user to record the corresponding prompt. In the absence of such a recording, the system uses text-to-speech synthesis.

Badge ID

This field gives the ID number of the badge currently assigned to the given user, if any. The ID is actually a ten-character alphanumeric encoding the unique physical (MAC) address of the badge. A badge can be assigned either by explicitly entering the ID into the field, or by voice command, as described later in the section entitled Badge Assignment. Note that in some environments, the MAC addresses of the badges may need to be explicitly registered with the wireless LAN access point(s) or RADIUS server as part of the security regime.

"Away" Messages

This stores recorded messages a user can elect to have played back to the caller when not available. A particular message can be selected either through the console or via voice command.

The announcement options page will now be described. This page presents the user with various choices controlling interaction with the Genie and notifications of different events.

Genie Persona

Users can choose the Genie personality with whom they will interact from among a number of different genders and personalities, including male, female, and even HAL-like voices. The choice of Genie controls not only the voice and personality in which verbal prompts are recited, but also various signaling tones, such as the "earcon" that announces that the Genie is listening. Note once again that in many vertical markets, users may not have access to the application, and a choice of persona may be made once and for all by the system administrator. The Genie Persona choice is presented on the page as a radio button group. Each button is accompanied by a label giving the name of the persona, and a button the user can click on to hear an introductory message from the Genie.

Genie Greeting Radio Group

This option allows the user to select how the Genie that he is listening for a command when the activate button is pressed. The control offers three alternatives:

Tone Greeting
Spoken Greeting
Tone and Spoken Greeting

In the first case, only a tonal "earcon" is played. In the second, only a persona-specific spoken phrase is played (such as "Vocera", or "Good Morning, Bob") is played. In the last case, the tone is played followed by the spoken phrase.

Verbal Genie Greeting Checkbox

If this option is elected, the Genie announces his presence with a spoken phrase (such as "Vocera", or "Good Morning, Bob") after the Genie earcon is played. If not, only the earcon is played.

Call Announcement Tone

This control is a drop-down box from which the user can select the sound to play to announce an incoming call. Note that this selection is independent of the Genie selection. Once again, a button is provided to allow the user to hear the selected prompt. At the same time that the call announcement tone is played, the name of the caller is displayed (if ascertainable) on the LCD. The system may permits customized ring signals to be used for different callers such that a particular caller may have a particular ring tone associated with him/her.

Verbal Announcement Checkbox

If this option is elected, incoming calls are announced verbally by the Genie after the call announcement tone is played: "Can you speak to John Smith?" for example. If the auto-answer feature (see below) is enabled, the verbal prompt is an announcement as opposed to a question: "Here is John Smith".

Auto Answer

Ordinarily, it is necessary to take an explicit action to accept an incoming call. This can be done either verbally (for example, "Accept") or by pressing the activate button. The call can also be explicitly rejected, either verbally or by pressing and holding the activate button. If verbal call announcement is not selected, a call can also be rejected implicitly simply by not answering. Note that incoming calls can thus be accepted (or rejected) in a completely hands-free manner.

By electing the auto answer option, the call is put through without explicit acknowledgement. If verbal call announcement is currently enabled, the Genie simply says, "Here's Johnny!" rather than "Can you speak to Johnny?" Auto answer is useful when a team is engaged in frequent communication, and maximal efficiency is desired.

Auto "Who Called?"

If this option is elected, the Genie will automatically, upon invocation, say who called or left messages. More precisely, the Genie will recite the names of users who unsuccessfully called or tried to deliver a message since the last Genie invocation: "You had a call from Jim Jones and an urgent message from Jack Smith." The user can then issue verbal commands to retrieve any messages, or to call back whoever had called.

On/Off Network Alert

If this option is checked, an audible alert is signaled when a badge enters or leaves the network. This is most useful in environments wherein users are expected to turn in their badge prior to leaving the premises. Network status/signal strength is also indicated on the LCD display.

Low Battery Alert

If this option is checked, a tone sounds periodically when a low battery condition is detected. Battery condition is also indicated on the LCD display.

Misplaced Badge Finder

When this checkbox option is enabled, the badge emits a periodic sound, enabling its location to be ascertained if it is within the network. This feature will work only if the badge is within the network neighborhood and if the batteries have not yet run down.

Text Message Announcement Method

This setting specifies how the user's badge "rings" in the event of an incoming text message.

The options are:
1) Verbal announcement ("You've got text!")
2) Various ringing signals (courtesy tones, ringing signals, melodies, etc.); and/or
3) None In all cases, the LCD will display the name of the calling party (if known) and the LED will blink fast green.

The call screening options page will now be described. The call screening options determine whose calls are allowed through when the user is reachable (i.e., within the network neighborhood and not in do-not-disturb mode.). By "allowed through", we mean only that the call is announced; it may still be rejected—for example, simply by not answering. Calls that are not allowed through are handled according to the setting of the Forwarding Options described below.

Call screening entails selection from among two primary options, presented in as a radio button group:

Accept All Calls

This option effectively turns off call screening, allowing calls from everyone, including those who may be calling in from the outside.

Block All Calls

This option, at the opposite extreme, allows no calls.

In addition to selecting from the two primary options, a user may add or remove entries from an exception list. As the name implies, the exception list enumerates individual users and groups of users that represent exceptions to the primary selection. For example, if Block All Calls is selected, and Tech Support is added to the exception list, then calls from anyone in Tech Support are accepted. Similarly, if Accept All Calls is the primary selection, then adding Tech Support to the exception list blocks calls from anyone in Tech Support.

These call screening options, including manipulation of the exceptions list, can be controlled by voice command as well as through the browser application. For example, the command "Block all calls except from Steve Loscatoff and Randy Nielsen" causes the primary selection to be Block All Calls, and causes Steve and Randy to be placed on the exceptions list. The command, "Accept calls only from Steve Loscatoff and Randy Nielsen" has exactly the same effect. Now, the buddy list page will be described.

The buddy list page permits a user to generate/manage his/her buddy list. The buddy list is a list of parties with whom the user frequently communicates, and whose calls will normally be accepted, if not blocked by one of the call screening options enumerated above. A user's buddies each have a nickname that can (optionally) be used in voice commands in place of the buddy's full spoken name. By default, the nickname is just the buddy's first name. However, the user may specify any name he wants—for example, "Butch", "Maverick", or "Boss". Note that the nickname is private to the user, so that different users may assign a different nickname to the same person. For example, John may be on Mary's buddy list and Gina's buddy list, but may be called "Jack" by Mary, and "Johnny Baby" by Gina.

A buddy may be assigned VIP status. If given this status, the buddy can break in to the user in an urgent situation even if he would otherwise be blocked by dint of one of the call screening options—even if the user is in do-not-disturb mode at the time. In such a situation, the buddy is asked by the system whether the call is urgent. If he answers affirmatively, he is allowed through; otherwise, the normal unanswered call procedure is followed (see Forwarding Options).

In addition, a call announcement option may be elected for each buddy. In this way, the user can know who is calling on the basis of the tone announcing the call. The election overrides the general Call Announcement Tone setting.

A user's buddy list may include named groups as well as individuals. For example, putting Tech Support on your buddy list will insure that the tech support folks will always be able to reach you. Adding a group to the buddy list is tantamount to adding each member of the group to the list. The buddy list may also include outsiders (i.e., non-users), such as external business associates, friends, or Mom. When an outsider is designated as a buddy, a phone number and e-mail address can be filled in. The phone number allows the buddy to be dialed by name ("Call Mom"), and the e-mail address allows the buddy to be sent an e-mail with a voice message attachment ("Send E-Mail to Mom").

The buddy relationship is not necessarily reciprocal; for example, the fact that the boss has added Mary to his buddy list does not imply that the boss is on Mary's buddy list. However, in many team situations, being a buddy is a two-way street. The following two options are provided for convenience in such situations:

Automatic Buddies

If Mary elects this option and John adds Mary to his buddy list, then John will automatically be added to Mary's buddy list.

Automatic Notification

If Mary elects this option and John adds Mary to his buddy list, then the next time that Mary accesses her user console, she will be notified that John has added her to his list, and can choose at that time to add John to hers (or not). Note that in the case of a team, it may be most convenient to create a named group (see Named Groups below); the name of the group could be entered into each user's buddy list.

Note that in the case of a team, it may be most convenient to create a named group (see Groups Page below); the name of the group could be entered into each user's buddy list. The voice commands for call screening can refer to buddies explicitly, as in, "Block all calls except from Buddies", or "Block only calls from Buddies."

The forwarding options page permits the user to customize the forwarding options of the wireless communications system. Forwarding options come into play when a call cannot get through, either because the user is currently not within the network neighborhood, or because the call is blocked or refused. The system first checks the forwarding options to see whether the unanswered call should be forwarded to a phone number or to some other user's badge (such as that of an assistant) or to a group. If so, an attempt is made to forward the call. If the forwarding is successful, no further action occurs. Success, in this case, means that the call was answered, even if by an answering machine or voice mail. (In the case of forwarding to another badge, success means that the person to whom the call was forwarded was available and accepted the call). If no forwarding is specified, or if forwarding was not successful, the user's greeting is played (if one was recorded), and the caller is asked whether he wishes to leave a message. The forwarding options are presented as a group of radio buttons. Note that the desk phone number, cell phone number, and home phone numbers will need to have been specified in the Basic Information Page.

No Forwarding (default choice)

Forward to Desk Phone

If this option is elected, the call is redirected to the user's desk phone extension. From there, it may be picked up by the customer's voice mail system.

Forward to Voice Mail

In this case, the desk phone does not ring, but instead, the call is routed directly to the user's voice mailbox Forward to Cell Phone This option is similar to "Forward to Desk Phone" option, except that the user's cell phone number is dialed instead.

Forward to Home Phone

Forward to Another Number

If this option is selected, a text field must be filled with the number to be called.

Quick Message

The caller is prompted for a short (no more than 10 seconds) message. As soon as the user becomes available (is within the network neighborhood, and is allowing calls from the caller), the system automatically calls the user and plays the message.

Record Message for Voice Mail

This option makes it possible for a voice mail message to be left without going through the tedium of interacting with the user's voice mail system. Instead, the caller is immediately prompted for a message. Afterwards, the system calls up the user's voice mail box and plays back the message "behind the scenes" without the caller's having to wait.

Forward to Badge

If this option is selected, a user or group to which to forward the call must be designated. Forward to Badge might be used, for example, to redirect a call to an administrative assistant.

Voice-Enabled E-Mail

The caller is prompted for a message, which is then attached to an e-mail and sent to the user.

Voice-To-Text

The caller is prompted for a message, which is then transliterated to text and sent to the user, either through the network or through the pager service.

All of the forwarding options can be invoked using the Forward voice command.

The groups page permits the user to customize the groups feature of the wireless communications system. In particular, it is often convenient to name groups of users that can be referred to collectively. Groups often reflect organizational structure (Marketing, Tech Support, Security), and individual roles (Managers, Cashiers), but may also serve other purposes, such as to identify extemporaneous project teams. Group names can be provided as name arguments in most voice commands that take name parameters, can be entered in buddy lists and can have forwarding options just as ordinary users can.

The Groups Page provides the functionality needed to define and manage groups. It has means for creating or deleting groups, for adding or removing members, and for defining scheduling procedures when a group member is to be dispatched. System administration options control which users may perform these operations. The groups may also include a private group, which is visible only to the user who creates the group. The Groups Page contains the following controls and fields:

Group Selector

This control is a drop-down box that lists the names of all groups. When a group is selected from this list, the remaining controls on the page show information pertaining to that group.

New Group Button

This button, used to define a new group, is enabled only if the user has group-creation privileges. When pressed, the controls on the rest of the page are cleared to permit definition of the new group.

Duplicate Group Button

Operation is similar to New Group, but copies over settings from the previously selected group.

Delete Group Button

This button, which deletes the currently displayed group, is enabled only if the user has group deletion privileges. A confirmation dialog is presented when the button is pressed. (Note, however, that as with all other pages, changes are saved only if the Save button at the bottom of the page is pressed.)

Group Name Field (*)

This text field defines the name of the group as it appears in buddy lists, etc. The group name should reflect the collective form of the name of the group, as in Managers, Cashiers, Technical Support, Marketing.

Spoken Name Field

By default, the group name also serves as the spoken name. This field allows a phonetic pronunciation to be designated instead. The spoken name should give the collective form of the group. The Record Group Prompts voice command can be invoked to record a prompt vocalizing the name of the group. In the absence of such a prompt, text-to-speech is used.

Spoken Member Name Field

This field gives the spoken name of a member of a group. For the Tech Support group, for example, this field could be filled in with "a technical support agent." For the Cashiers group, it would likely be filled in with "a cashier". If the group defines a role that is occupied by only one person at a time, the prefix "the" should be used rather than "a". For example, if a store has only one Store Manager on duty at a time, "the store manager" should be used.

Spoken Member Name Field—Plural Form

Similar to Spoken Member Name, but gives the plural form. For the Tech Support group, for example, this field could be filled in with "technical support agents." For the Cashiers group, it would likely be filled in with "cashiers". If the group defines a role that is occupied by only one person at a time, this field should be left blank. The Record Group Prompts voice command can be invoked to record prompts vocalizing the spoken names just described. In the absence of such prompts, text-to-speech is used.

Scheduling Algorithm

When a user says "Call Tech Support", he does not wish to speak to everyone in tech support, but rather to any Tech Support person who is currently available. The scheduling algorithm determines the order in which group members will be checked for availability. The following choices are offered as a radio group:

Sequential Order

Members of the group are always tried in the order in which they appear in the group membership list. This algorithm is useful in environments in which one of the members takes primary responsibility for answering calls, but for which back-up members are named.

Round-Robin Order

Members of the group are tried in a rotational order. A time stamp is maintained for each member, so that the person who least recently took a call is the first one tried in the current round. This algorithm is useful in environments in which it is desirable to spread the load in a fair manner.

Membership List

The membership list is a table that displays all the current members of the group, and possibly a time stamp giving the last time the member took a call as a member of the group. Group members can be either individuals or other groups. Groups can thus be nested within other groups. For example, the House Keeping group might be a member of the Guest Services group. Rows of the membership list can be selected to facilitate the member operations listed below.

Member Add/Delete

Buttons are provided to add a new member, as well as to delete the currently selected member(s). Pressing the Add button brings up a dialog from which a new user or group can be selected as a new member.

Member Reordering

Because scheduling works with respect to the order of members in the Membership list, it is useful to be able to change the ordering of members in the list. Move Up and Move Down buttons are provided for this purpose, and cause the currently selected member to be moved upward or downward, respectively, in the membership list.

Forwarding Options

Voice commands can also be used to allow users to add or remove themselves from a group. A user simply says, for example, "Add me to group Tech Support", or "Remove me from group Tech Support". In the event he is a member of more than one group, the Genie will ask for the name of the group. Adding and removal in this way requires a permission defined on the User Administration page of the administration browser application.

Voice commands are also provided to list the members of a group ("Who is in Tech Support?") and to list the groups of which a user is a member ("What groups am I a member of?") or to enumerate all of the existing groups in the system ("List all Groups"). The Groups Page can be made invisible to non-administrators through a system administration option. In this case, the Groups menu button will simply be omitted from the page selection menu.

The groups page may further include the following features.

Locate Enabled Option

This option controls whether the user will allow himself to be located when within the network neighborhood (see description of the Where command). The user may wish to turn this off for privacy reasons (if system administration policy permits).

Auto "Who Called?" Option

If this option is elected, the user is automatically notified as to who tried unsuccessfully to reach him. The notification occurs when the user next activates his badge.

Logging and Archive Options

These options control:

Logging of calls and text messages

If enabled, the console maintains a log of call and message activity. The log shows the date, time, and originator (including phone number of an outsider caller, if determinable) of each call or pager message.

Save Messages

If this option is selected, text messages will be automatically "uploaded" from the badge periodically and saved. Controls are provided in the console for viewing and deleting these archived messages.

Genie Prompt Options

When the user summons the voice recognition system (the Genie) by activating his badge, a prompt is played to signal that the Genie is listening. This option allows the user to choose from among a number of prompt options, including:

1) Verbal Prompt (such as "Vocera—how can I help you?"); and/or

2) Various courtesy tones.

Electing this option makes the voice command prompts more verbose. The verbal commands are unchanged, but the user is "babied" more.

Predefined ("Canned") Text Messages

Predefined, or "canned" messages provide a means by which a user can reply to messages or calls from other users simply by making a selection from the badge display menus. See the "Text Messaging" section for a more detailed description of this feature.

Learn Mode Option

Electing this option makes the voice command prompts more verbose. The verbal commands are unchanged, but the user is "babied" more.

Power Control Options

These may include, for example, restricted hours of operation that save battery power.

Pager CAP Code

This field gives the CAP Code assigned to the user. As with the Badge Serial No, this field cannot be set by the user. It will instead be set either by the system administrator, or will already have set inside the badge itself at the factory. Now, the badge assignment process in accordance with the invention will be described in more detail.

Figure 8A:
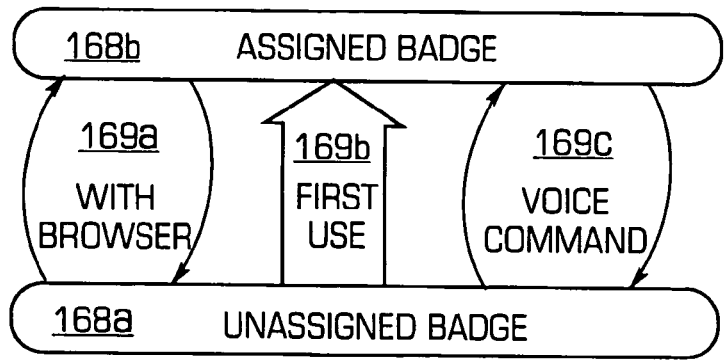
FIG. 8A illustrates the badge assignment methods in accordance with the invention.

FIG. 8A illustrates the badge assignment process in which a badge may be in an unassigned state 168a or an assigned state 168b. The assignment/unassignment process may be carried out with a browser 169a, with first use 169b and with voice commands 169c. In more detail, the system must be aware of which badge each user is wearing so that calls can be properly routed. Badge assignment is the process of associating a badge with a particular user. At any given time, a badge can be assigned to at most one user, and each user can have at most one badge assigned. Note that each badge is uniquely identified by a Badge ID that encodes its network MAC address. Assigning a badge to a particular user is therefore tantamount to assigning a Badge ID (MAC address) to that user. If the user leaves the network boundary (and loses connection with the network) and then returns to the network, the badge will send its MAC address to the server 36 when it returns to the network and the system will be able to automatically re-associate/re-assign the badge back to the user based on the MAC address of the badge by looking up the MAC address in the user profile database to locate the user.

A number of ways of assigning a badge are provided in order to accommodate different customer requirements. In some cases, the system administrator or the user himself may wish to pre-assign badges at the time the user is added to the system. In other environments, badges will be shared or allocated from a pool at the beginning of a shift. In this latter case, assignment will more likely be performed dynamically through the "Log On" voice command.

When a badge is assigned, the name of the user is downloaded to the badge at the next opportunity, and is displayed on the LCD when no conversation is in progress. (If a badge is not currently assigned, the display shows the Badge ID.) In addition, user badge preferences stored in the user profile database, such as a network boundary alert or a battery low alert, may be downloaded to the badge so that the particular badge currently assigned to the user will operate according to the user's badge operation preferences. The assignment also causes any text messages that had been previously stored in the badge to be cleared, and any text messages available for the user to whom the badge is assigned to be downloaded automatically. From the user's point of view, his messages "follow" him. If a badge becomes unassigned (via one of the methods described below), the messages are cleared. Following are descriptions of the different methods of assigning and un-assigning badges:

Assignment/Unassignment through the Browser Application

A badge can be assigned by explicitly entering its ID in the Badge ID field of the Basic Information Page. If the badge was previously assigned to a different user, a warning message is issued. The badge can be unassigned simply by clearing the field, or by reassigning its ID to a different user.

Assignment on First Use

If the badge is unassigned at the time the Genie is hailed, the Genie will greet the user and ask the user to say his name. If the name is recognized, the badge will then be assigned to the user. Note that the assignment will work only if the user had been previously registered in the system. The assignment may also be predicated on a successful match of the voiceprint of the user, using the verification feature of the speech recognition system.

Assignment/Unassignment by Voice Command

At any time, the badge can be reassigned dynamically using the "Log On" voice command. Once again, the reassignment will work only if the user has been previously registered in the system. And once again, if voiceprints are used, a successful match is required. Badges can be unassigned using the "Log Off" voice command. Note that in each case, the bearer of the badge must first be registered with the system (or be registered by the administrator) before the badge can be assigned to him. In cases where visitors may be provided with a badge to be used temporarily, it may be useful for-the administrator to register a few "Guest" users (the registration process only takes a moment) and assign guest badges to them. If desired, the spoken name of the guest can be entered through the user console, so that other users can hail him by name as opposed to an appellation such as "Guest Three". Now, the operating states of the communications badge in accordance with the invention will be described.

Figure 8B:
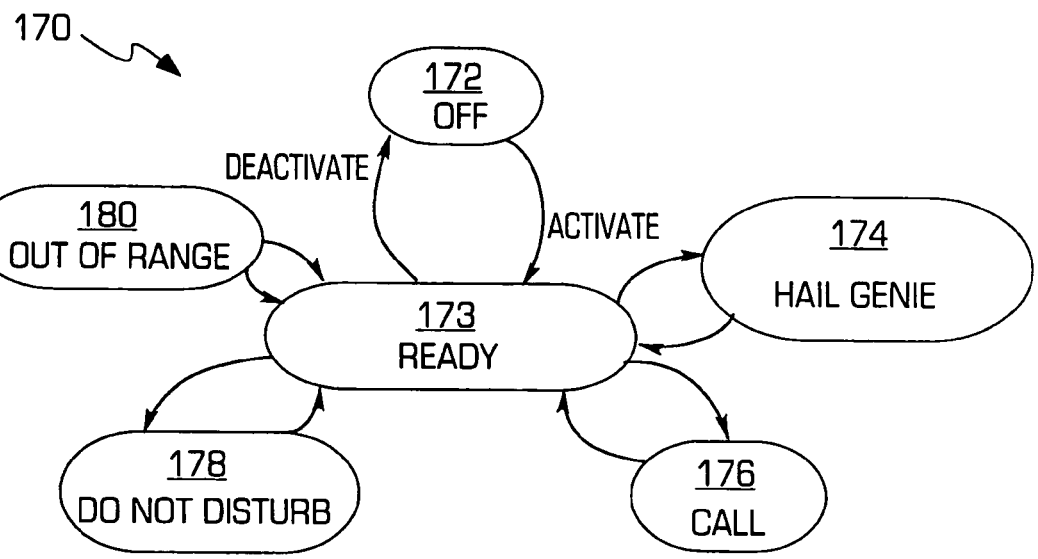
FIG. 8B is a state diagram illustrating the preferred operating states of a communications badge in accordance with the invention.

FIG. 8B is a state diagram 170 illustrating the preferred operating states of a communications badge in accordance with the invention. The operating states may include an off state 172 in which the badge is not operational and a ready state 173 in which the badge is ready to be used but in not currently being used for any purpose. The states may further include a hail genie state 174 as described below, a call state 176 as described below with reference to FIG. 10, a do not disturb state 178 as described below and an out of range state 180 when the badge is not within the network neighborhood.

To move from the off state to the ready state, the badge is activated and to move back to the off state, the badge is deactivated. When the user wishes to initiate a call or other interaction with the server 36 (i.e., the Genie), he must explicitly activate the badge by pressing the activate button. Note that for reasons of power conservation and other resource constraints, the voice recognition server cannot be listening all the time—one cannot wake it up simply by uttering some magic word. Moreover, it is quite important that a user understand when the microphone is active and when it is not. For these reasons, explicit activation is used to initiate an interaction. A badge may, however, be activated automatically as a result of an incoming call from some other party. Automatic activation requires that the badge be powered on at the time.

Upon activation, a sound prompt called an earcon is played alerting the user to the fact that the Genie is now listening. The earcon is a function of the Genie persona configured in the browser application. If activation is unsuccessful because the user is not currently within the network neighborhood, a prompt is played informing the user. Once the Genie earcon is played, the user can interact with the server through voice commands. Command dialogs other than those that result in the establishment of a conversation with other people are automatically terminated by the Genie. The Genie will simply say "Good Bye", or some such, and the user will not need to take any further action.

If the interaction with the Genie results in the establishment of a conversation with other people, the Genie bows out and the parties are left to converse. No further pushbutton action is likely to be needed until one of the parties wishes to disconnect. This is done with another press of the activate button, which causes the badge to revert back to the standby state. Disconnection occurs without having to explicitly press the activate button in each of the following circumstances: In the case where a call is in progress, and all other parties to the call disconnect, the remaining party is automatically disconnected without having to press the button. In the event that the radio link fails because the user wanders outside coverage of the network for more than a several seconds grace period, disconnection occurs. Disconnection is always accompanied by a prompt informing the user as to what happened.

Note that a press action is used to initiate a call, and a press-and-hold action is used to explicitly disconnect. More generally, the press action is always used as a positive or initiating action, whereas press-and-hold is always used as a negative, or canceling action. Press is used not only to initiate a session with the Genie, but also to accept an incoming call, to save a message or greeting that is being recorded, and other affirmative actions. Press-and-hold, on the other hand, is used not only to terminate a call, but also to reject an incoming call, and to cancel the record or play of a message or greeting in progress.

Using a simple positive/negative semantic rule for these actions not only makes it easier and more intuitive to use the system, but also makes it possible to respect a design principle requiring that the same command action be used to achieve a particular result across all contexts. So for example, if pressing the activate button again (as opposed to pressing-and-holding) were used to terminate a call, then the means used to hail the Genie or accept an incoming call would need to change depending on whether or not a call was in progress. This would likely result in users inadvertently disconnecting their call when they were expecting to hail the Genie.

Placing a Call on Hold

During the course of a call, a user may be approached by other people who may not be aware that a conversation is in progress. Conversely, the user may wish to consult privately with someone else in the room. In such cases, it is desirable to be able to place the current call on hold quickly and easily. A hold button is conveniently located at the top of the unit for this purpose. To place an ongoing call on hold, the user simply presses the hold button. A verbal prompt announces that the call is being placed on hold, and the hold button illuminates. The other party to the conversation, for his part, hears a prompt politely asking him to hold. In the case of a conference call, however, the remaining parties hear a tone warning them that a party has left the conversation, but can continue to talk. Similarly, if a conference is rejoined, the remaining parties hear a tone warning them that another party has entered the conversation. Having placed the call on hold, the user can no longer hear nor be heard by the other party.

To return to the conversation, one simply presses the hold button a second time. He will then hear a prompt confirming that he is rejoining the call. The holding party is similarly notified, and the call continues. While a call is on hold, the user may wish to hail the Genie by pressing the activate button. A description of what transpires in that case is given in the section labeled Hailing the Genie below. Note that if the original call is disconnected for some reason in the meantime (because, for example, the other party disconnected, or the user who placed the call on hold wandered outside the network neighborhood), then the hold mode is terminated, and the disconnect prompt is played.

Do-Not-Disturb (DND) Mode

If pressed while no call is in progress, the hold button places the badge in a mode in which all calls are blocked. The hold button blinks to signal the mode. This feature provides a quick and silent method for a user who is entering a meeting, for example, to insure that he will not be disturbed. The semantics are similar to the Block All Calls screening mode. Thus, buddies with VIP status will still be able to reach the user in the event of an emergency. The mode can later be left by pressing the hold button a second time, or by pressing the activate button to activate the badge. In principle, one could allow DND mode to continue even if the badge is activated. This would clash with the use of the button to place calls on hold, and would require different interactions for Hold and DND, thereby complicating the use of the button. Since activating the badge likely means that the user is now out of his meeting, it is probably acceptable that this action ends the DND mode.

Hailing the Genie

As described earlier, pressing the activate button while the badge is inactive summons the Genie. If the dialog with the Genie results in the successful establishment of a connection with another party or parties, the Genie bows out of the conversation and the speech recognition port then becomes free to serve a different user. The user may wish, however, to regain the attention of the Genie in the midst of the conversation—for example, for the purpose of conferencing in another party. To hail the Genie without terminating the current call, the user places the current call on hold, and then presses the activate button again. This action will invoke the Genie. Once the interaction with the Genie has concluded, the user will rejoin the conversation in progress automatically. The user can terminate interaction with the Genie (and rejoining the call on hold) at any time by pressing the activate button, or by uttering the "Good Bye" voice command. The case in which the user initiates another call while the first call is on hold is described momentarily. Now, the Genie commands will be described in more detail.

Genie Commands

The design of the voice command system is such as to strike an appropriate balance between flexibility of expression, on the one hand, and predictability on the other. Another balance to be struck is that between economy of expression and ease of learning. Given that the application is used every day, elaborate dialogs and confirmation protocols for frequently used commands are to be avoided. To accommodate the learning process while retaining economy of expression, both a verbose learning mode and a-less prolix high efficiency mode are supported, and are selectable from the User Console.

Command Syntax

For the most part, voice commands have a simple "verb object" structure. For example, "Call John Smith" is typical. Commands keywords for the most common commands may have synonyms. For example, instead of "Call John Smith", one could say "Get me John Smith", or "Find John Smith".

Noise Words

Certain "noise" and "hesitation" words may be used as well. One might say, for example, "Um, Vocera, please get me John Smith". Naturally, there are limits to the tolerance for variations. The system may not recognize "Where the **** is John Smith!!".

Name Arguments

In general, commands that include user names and group names as arguments to respond to one of the spoken names registered for that user or group in the browser application. However, if the party in question is included on the buddy list of the caller, the nickname listed for that buddy may be used instead. Spoken names and buddy nicknames may not be unique. In the event of ambiguity, the Genie will ask the user which of the possibilities he means by playing back the spoken name recorded for each possibility. If two users have exactly the same full name, the identifying phrase set in the Basic Information page of the browser application can be used to disambiguate. Most commands that take name arguments allow up to three names to be cited. In this case, the names must be separated by "and", as in "John and Mary", or "John Jones and Mary Bush and Jim Smith". Group names may be used as well, as in "Leave a message for John and Tech Support." If the Genie has trouble recognizing the name or names spoken in a command, it may ask the user to choose among the most likely possibilities.

Recording of Name Prompts

Individual users, groups, identifying phrases, and access point locations can have associated sound files that are played by the Genie in course of a dialog. A set of voice commands is provided to enable recording of these prompts. In case the prompt associated with a particular entity is missing, TTS (text-to-speech) is used instead. Because the state-of-the-art of TTS synthesis, especially in the case of names, is less than perfect, users and system administrators should be encouraged to record names for most purposes.

Universal Commands

Universal commands are those that can be uttered whenever the Genie is listening. The following universals are supported:

Help—This command calls for context-sensitive help, including the possibility of interaction with a human technical support agent at the wireless communications system.

Cancel—This command cancels the current command.

Quit—The command deactivates the badge.

Goodbye—terminates interaction with the Genie.

Emergency—This command, after confirming, calls "9-1-1".

Barge-In

"Barge-in" refers to the ability for a user to break in with a command while the Genie is playing a response, without having to wait for the prompt to complete. Barge-in will be supported to the extent possible. Now, the calling and message features of the system will be described.

The system supports a number of calling modes and features, including multi-party calls, conferencing, call waiting, call forwarding, and call transfers. A number of messaging features are provided as well, including voice message broadcast, and text messaging. Features are also included that allow the current location of users to be determined. A descriptions of these various functions in the form of scenarios, starting with basic calling, and progressing through more advanced calling features, messaging, and location will now be described. In particular, a badge to badge communications session and then the other call states will be described in more detail.

Figure 9:
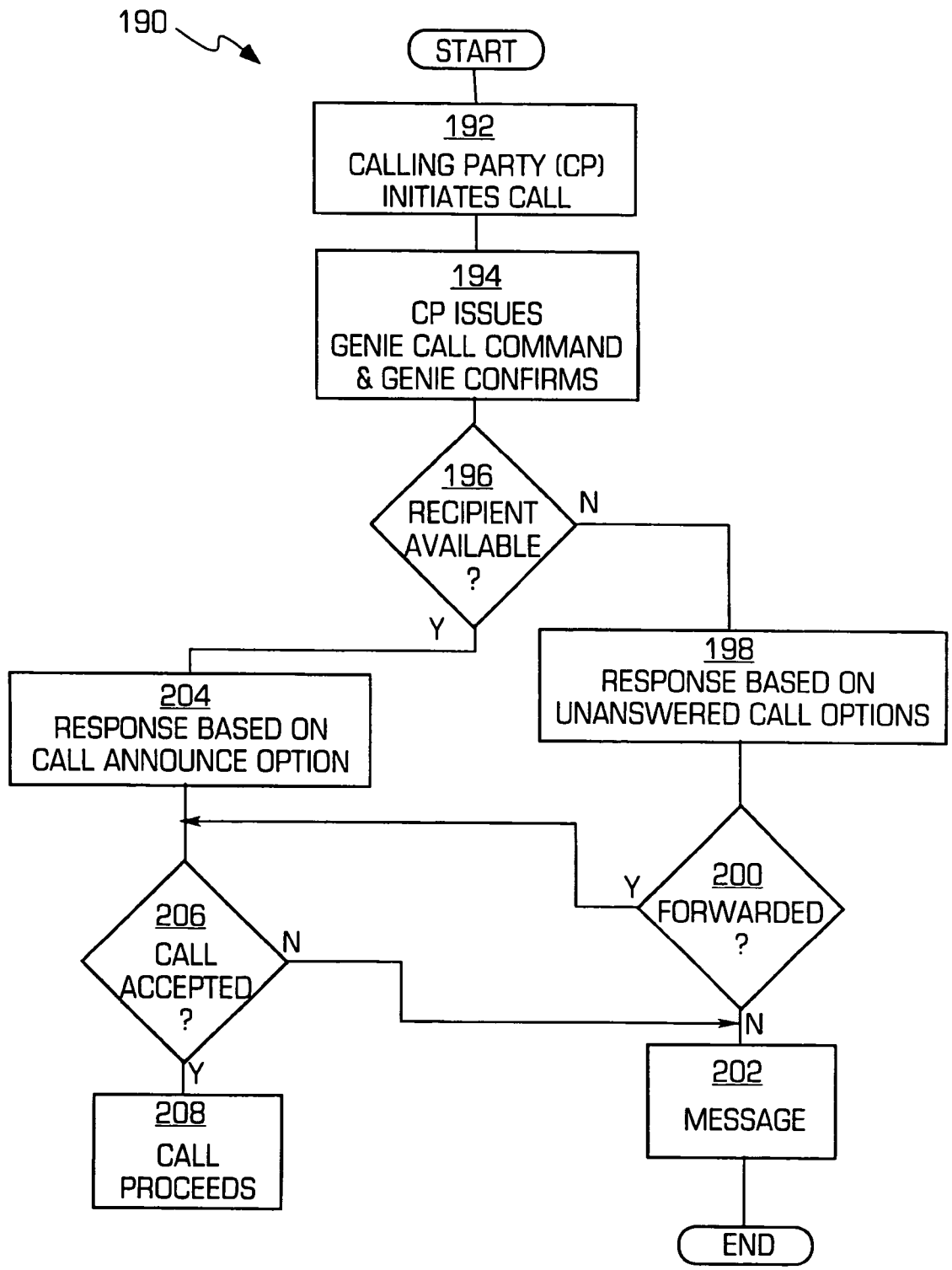
FIG. 9 is a flowchart illustrating a method for performing a badge to badge communications session in accordance with the invention.

FIG. 9 is a flowchart illustrating a method 190 for performing a badge to badge communications session in accordance with the invention. In step 192, the calling party (let's call her Mary) initiates the call by pressing the activate button to summon the Genie. Upon hearing the Genie prompt, she issues a command in step 194, such as, "Call John Smith", or "Get me John Smith", where John Smith is the spoken name of the called party. If John Smith is on the caller's buddy list, John's nickname can be used instead: "Get Jack". The Genie confirms the command by replying, "Finding John Smith . . . " wherein the "John Smith" part is played in John's own voice. If the server incorrectly recognizes John's name ("Finding Joan Smith . . . "), Mary can simply say, "Cancel" and reissue the Call command.

In step 196, the server 36 (using the user database) determines if the recipient is available. If the recipient is not available (e.g., If John is outside the network neighborhood or is currently blocking calls from Mary), the response in step 198 depends on the setting of John's Unanswered Call options. If John has specified a forwarding method (as shown in step 200), the call is automatically routed using that method; if John has specified one of the message recording options, Mary is asked whether she wants to leave a message (in step 202). Otherwise, Mary is told that John is unavailable but will be immediately notified of her call. The transaction ends, and Mary's badge is automatically deactivated.

Returning to step 196, assuming that John is currently available, and that calls from Mary are not blocked, John's badge signals an incoming call in the manner determined by his Call Announcement Method setting in step 204. In addition, Mary's name flashes on the LCD display. If John has set the Auto Answer option, the call is put through immediately. Otherwise, he accepts or rejects the call either verbally (e.g., "Accept"), or using the activate button (press to accept, press and hold to reject). John can also reject implicitly simply by doing nothing. Finally, he may decide to reject, but send a message back to Mary ("Tell Mary . . . "). If the call is accepted in step 206, the conversation between Mary and John begins in step 208 and the Genie drops out of the loop. If either party needs Genie services during the conversation, the Genie can be hailed by putting the current call on hold and pressing the activate button as described earlier. Either Mary or John can terminate the call by pressing and holding the activate button, causing both badges to be deactivated. If the call is rejected, John's badge automatically deactivates. If John used the "Tell" command to leave Mary a message, that message in step 202 is played back to Mary. What happens next on Mary's side depends on the setting of John's Call Forwarding options, as described above. As a shortcut, the call command can also be invoked simply by uttering the name of the called party without any verb. For example, Mary could simply say, "John Smith", rather than "Get me John Smith."

A badge to badge communications session may be viewed as a peer to peer communication. Normally, a badge will not compress the voice data being sent to the server 36 so that the quality of the voice commands to the voice recognition system are not degraded. However, if a badge-to-badge communications session is occurring, both badges will in fact compress the voice data to the other badge in order to reduce the amount of data being communicated between the two badges. If the Genie is communicating to the badge, the data will also be compressed. Now, the one or more different call states in accordance with the invention will be described in more detail.

Figure 10:
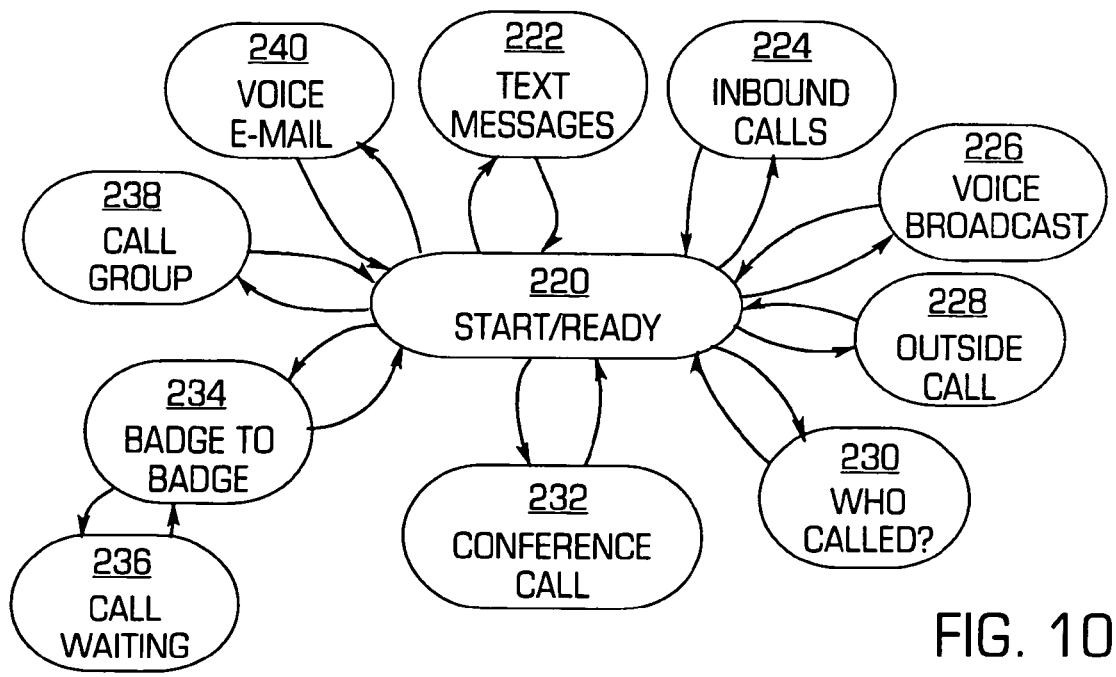
FIG. 10 is a state diagram illustrating the preferred call states of the wireless communications system.

FIG. 10 is a state diagram illustrating the preferred call states of the wireless communications system. The system supports a number of calling modes and features, including multi-party calls, on-the-fly conferencing, call waiting, message broadcast, and calls to and from the PSTN (public switched telephone network). The states may include a ready state 220 in which a call may begin, a test message state 222, an inbound call state 224, a voice broadcast state 226, an outside call state 228, a who called state 230, a conference call state 232, a badge to badge call state 234 as described above including a call waiting state 236, a call group state 238 and a voice e-mail state 240. Now, various of these call states will be described in more detail.

Conference Call State

If Mary wishes to initiate a conference call with Jim and John, she simply says, "Call Jim and John." The two parties will be called and conferenced together to create a three-party conversation. Conferences of up to four parties can be created in this way ("Call Jim, John, and Sam"). The interaction for conference calls differs from that for a straight two-party call in the following ways:

Parties that join a conference in session are alerted to that fact via a tone prompt;

Each new party is announced with a tone, alerting the others; and

If a party is unavailable, he is simply not included; forwarding of calls to voicemail, and other Unanswered Call options are inhibited.

A conference can also be initiated by adding parties to an ongoing conversation. If for example, Mary wishes to bring Jim into her conversation with John, she hails the Genie (by putting John on hold), and says, "Call Jim Jones" in the usual manner. Once she reaches Jim, she simply presses the hold button again. At this point, the Genie will ask if she wants to merge the two calls. If she answers "Yes", the three parties are now engaged. Note that if Mary just wanted to ask Jim a question, she could disconnect after speaking to Jim (by pressing the activate button), and would then be back to the original conversation. Note that if Jim were not available, the call to him would be forwarded in the normal way, or Mary could leave a message in the normal way.

Blind conferencing is even easier. Mary simply hails the Genie and says, "Invite Jim". The Genie acknowledges, and without further ado, Mary is back talking to John. Behind the scenes, the Genie calls up Jim much in the same manner as would have been the case had Mary called both Jim and John in the first place. Assuming Jim is reachable, he joins the conversation and tone prompts are played to the various parties apprising them of that fact. The interaction is said to be blind because Mary loses control of what happens if Jim is not reachable, and is also unable to have a private chat with Jim prior to Jim's joining the conversation. The ability to exercise this control is sacrificed for the greater efficiency of the command. If, in the future, it is determined that conferences with greater numbers of parties are needed, a special half-duplex conferencing feature can be added to accommodate this.

Call Waiting State

If, in the Badge-to-Badge scenario described earlier, John is already engaged in a conversation with another party, he will be alerted to Mary's call with an audible call waiting signal. In addition, Mary's name will be displayed on the LCD, and the LED will blink fast as with any incoming call. If John wishes to accept the call from Mary, he presses the activate button. He will then be speaking to Mary, and his current call will be placed on hold. When he is done speaking with Mary, he disconnects in the usual way (by pressing the activate button), and will then be back to the original call. The same thing happens if Mary explicitly disconnects. John can have Mary conferenced into his original conversation. To do so, he simply hails the Genie (by pressing the activate button as usual).

Call Transfer State

Call transfer allows an incoming call to be redirected to a different badge or outside number. Calls can be transferred in either a supervised or a blind manner. Supervised transfer is done simply by conferencing in the third party, and then bowing out of the conference. Suppose, for example, that John calls Mary, who then wishes to redirect the call to Jim. Mary puts John on old and hails the Genie in the usual way. She then attempts to call Jim. Assuming the call succeeds, she presses the hold button to join the three parties together, bids her fair well, and then presses and holds to disconnect. The two remaining parties are left to their own devices. If, of course, the attempt to reach Jim fails, Mary is back-to talking to John. Note that all this works because Mary—the middleman—can leave the conversation without terminating it. The same does not work with the typical telephone conferencing feature probably because no one is left to pay the toll for the path between Mary and Jim.

Blind transfer is more abbreviated. Mary hails the Genie and says, "Transfer to Jim." At this point, she is out of the loop, and the call proceeds very much as if John had called Jim directly in the first place. Blind transfer is less trouble for Mary, but makes it impossible for Mary to introduce John to Jim, or to help John if Jim can't be reached. A special transfer command, "Transfer to Voice Mail", may be provided as well.

Calls to a Member of a Group State

It is often useful to be able to call someone by function or title rather than by name. For example, Mary may need Tech Support, but not know (nor care) who is currently managing the help desk—she simply wants to be able to say "Get me Tech Support". The effect is easily accomplished by defining "Tech Support" as a group, and by designating one or more people as the members of the group. The Tech Support manager, might, for example, set up this group.

In many situations, the group might have only a single member. In this case, the group name serves as an alias for the person who is currently responsible for answering calls for the group. If the group has more than one member, the incoming call will be routed to the first person on the list who is available. In this way, alternates can back up the primary group representative. If the group has more than one member, the system will attempt to find the first member of the group who is available according to a scheduling algorithm that is specified in the group definition. See the Groups Page description in an earlier section for details.

Recording a Greeting

With the "Record Greeting" voice command, a user can record a message that will be played to callers who unsuccessfully attempts to call. To record a greeting, Mary invokes the Genie and says "Record Greeting." The Genie then prompts Mary to begin recording. When finished, Mary presses the activate button to indicate that she is done. She is then asked to confirm that she wishes to keep the greeting. She can also explicitly cancel the greeting while it is being recorded by pressing and holding. The greeting can later be erased (using the "Erase Greeting" voice command) or rerecorded.

Who Called? State

The "Who called?" voice command can be used to learn of parties who tried unsuccessfully to reach the user or left a message. After she is done with a meeting, for example, Mary might hail the Genie and asked "Who called?" The Genie might reply, "John, Sam Spade, and Mom called" or the Genie might reply, "You had a call from Mom and a message from John Brookes". Note that calls that a user misses for any reason are signaled on the LCD display even when the user is currently outside the network neighborhood. The "Who called" command is a quick way to get this information without having to manipulate the display. The "Who Called?" command can be automatically executed when the user activates his badge by setting the "Auto Who Called?" option in the User Console.

Voice Message Broadcasts State

This feature affords a means by which users can send recorded voice messages to one or more recipients. The most obvious uses of this feature are leaving a message for someone who is not currently available to speak, or to broadcast a message to a group. However, sending a message is also very useful when one doesn't have time for a call, but wants to quickly communicate a thought and get on with one's business.

The messaging is, in any case, a real-time communication mechanism—the moment a message is recorded, the system attempts to deliver the message to all messaged parties. Suppose, for example, that Mary wishes to leave a message for John, and for everyone on the Blowtorch team. She hails the Genie and says, "Send a message to John and The Blowtorch Team". The Genie then prompts her for a message ("Please record a message at the beep. Press the activate button when done.") Mary articulates the message, then either just stops talking or presses the activate button. The system will then ask for a confirmation ("Shall I send this message?"), and assuming the user agrees, sends the message. Having recorded the message, the system will immediately call each targeted user and play it back. Users that cannot be reached (because they are away from the network, or have blocked the call) are notified immediately upon becoming available. A user can then play back the message using the Play Messages command.

Note that the use of groups in this case has a different semantic than that for calls. If one says "Call Tech Support", at most one Tech Support person is called; if one says "Send Message to The Blowtorch Team", a message is broadcast to every member of the team. Naturally, calling a large group of people at once is challenging and the system only supports conferences with at most four participants anyway.

Messages that have been played are automatically deleted after a certain duration that can be configured from the System Options page of the administration application. A user can replay old messages any time prior to their deletion using the Play Old Messages variant of the Play Messages command. Messages will be played in most-recent-first order, with urgent messages played before non-urgent ones.

During the play of a message, a user may issue any of the following barge-in commands:

Save This command will inhibit deletion of the message until it is explicitly deleted using the Delete command below.

Delete—Deletes the message immediately.

Repeat—Plays the message again.

Next—Skips to next message.

A voice message can be marked as urgent, as in "Send urgent message to John Smith". In this case, assuming that the sender has VIP status, or is a VIP buddy of the recipient, message delivery will be attempted even if the recipient has a call in progress, or if it would otherwise be blocked.

Voice E-Mail State

This feature allows a user to send an e-mail with a voice attachment to the e-mail address of another user or users (or to outsiders on the buddy list). The interaction works similarly to Voice Message Broadcasts, except that the command is "Send e-mail . . . " rather than "Send message.

Outbound Calls State

Calls can be placed through the public phone system using the Dial command. For example, Mary might hail the Genie and say, "Dial area code six-five-oh eight-five-one-two-two-three-four". If an outsider has been set up as a buddy, a buddy name can be provided ("Call Mom") instead. Note that unanswered calls can also be forwarded to outside numbers (see Unanswered Call options above).

Inbound Calls State

Calls can also be accepted from the public phone system. In this case, the caller dials a phone number that reaches the system inside the customer premises (perhaps an extension on the customer PBX). The caller is then played a greeting, and is prompted by the system to say the name of the user to whom he wishes to connect. If caller id is not provided, the caller is also asked to identify himself ("Who may I ask is calling?) This information allows the called user to be prompted with the name of the caller, and allows the system to recognize the caller as a buddy. The call is then routed much in the same way it would were it to have been originated internally.

The caller can also enter the user's numeric identifier, such as an desk extension number, on the telephone keypad rather than pronouncing the user's name. To accomplish this mapping from the extension to the user, the system may first map the digit sequence to a user and then map the user name to the currently assigned IP address based on the user profile database.

Remote Dial-In State

This feature makes it possible for a user to treat his cell phone, for example, as if it were a badge. The user dials the system, as in the case of inbound calls. (The number would typically be set up as a speed-dial number.) Using caller id, the system recognizes the identity of the user, and hails the Genie. The user can now interact with the Genie in the usual manner. Pressing a key on the cell phone simulates the action of the activate button.

Text Messaging State

The text messaging feature makes it possible for badges to receive, store, and display text messages from a number of originating sources. Such messages might be sent by other users, but could also be sent automatically (such as by a nurse call center system), or in response to a future voice command queries of a database. For example, a user might ask for the detailed description and price of an item with a certain part number, or the medical history of a certain patient. The response to the query could then be displayed on the-screen of the badge.

The system will support these various applications using e-mail and possibly instant messaging as a transport mechanism. The server 36 hosts a POP3/IMAP mail client that serves as a forwarding mechanism for messages addressed to particular users. A standardized address convention is used for this purpose, based on the login name of the user. For example, to send a message to Julie's badge at Home Depot, one would simply address an e-mail to vocera@homedepot.com with "julie" (Julie's login name) as the subject of the e-mail.

When a message is received on the server, it is immediately downloaded to the target badge. If the badge is not currently within the network neighborhood, the download occurs the next time the badge reenters the neighborhood. Upon receipt on the badge, a tone is played to announce the arrival of the message. In addition, the status LED blinks to indicate that a message is pending. New and old stored messages can be accessed at any time through the badge menu system, as described in detail in a later section.

Because the messages are stored locally in flash memory, they can be perused even when the badge is outside the network neighborhood. The local message store will have sufficient capacity to store at least twenty 200-character messages. When the capacity of the store is exhausted, old messages are automatically deleted in the order in which they arrived. If the badge is logged out, the message store is automatically erased for privacy reasons. Similarly, upon assignment to a different user, the messages for that user are automatically downloaded to it.

Missed Call Notifications State

When an incoming call is missed, either because the user is currently outside the network neighborhood, or has blocked or rejected a call, a text record of the missed call is sent to the badge. If the user is outside the network, the record is sent though the paging service; otherwise it is sent through the network. The record consists of the date/timestamp of the call, as well as the name or caller id (if determinable) of the caller. It is accessible through the Messages screen selectable through the badge menu system.

Predefined ("Canned") Replies State

A message replies that have been pre-specified in the User Console (e.g., "Yes", "No", "OK", "Call you later") can be originated through a badge menu selection. This feature makes it possible to respond silently to a call or text message received while in a meeting, and provides some of the functionality offered by two-way pagers. The user selects the incoming message in question from the Message List accessible from the Main badge menu, and chooses "Reply" from the pop-up menu. He is then presented with a submenu listing the various predefined responses, from which he selects one.

Voice-to-Text State

This feature permits voice messages to be transliterated to text and sent to a user's badge either through the network or through the paging service. The voice-to-Text could be implemented either completely automatically (using dictation speech recognition software) or manually using a behind-the-scenes human service. The feature is accessed through a voice command. The user would hail the Genie and say "Send Text Message". He would then be prompted for the message (much in the manner of Voice Message Broadcasts), which would then be sent out. If the Voice-to-Text option is selected in the User Console as an Unanswered Call option, a caller could be prompted automatically for a message if the target user is not available. Now, a method for locating a user of a badge in accordance with the invention will be described in more detail.

Automatic Location of Users

The system provides a way to determine whether or not a user is currently within the network neighborhood and to pinpoint his whereabouts (within the resolution of an access point) in the event that he is within the network neighborhood. To accomplish this user location, a "Locate Enabled" option must be enabled on the system options page of the administrator application described above. The location ability also requires that the access points be identified with designations that will be meaningful to users—for example, "Building C, $2^{nd}$ Floor, Left Wing". The system may include the ability for the system administrator to configure the access point designators using the access point locations page of the browser application described above. The system may also provide two voice location commands. One command permits the user to ask the system to determine the location of a particular user and the other command permits the user to ask the system to determine the user within a named group that is closest to a given location (e.g., I need a tech support person who is near my location). The following are examples of the use of these commands:

User: "Where is Jim Jones?"
Genie: "Jim Jones is in Building C, 2$^{nd}$ Floor, Right Wing
User: "Where is Mary?"
Genie: "Mary is currently on the Santa Clara campus in the Cafeteria"
User: "Where is Mary?"
Genie: "Mary is currently off campus."
User: "Who in Tech Support is in Building C?"
Genie: "Brad Jones and Jerry Peters are in Building C"
User: "Where is the closest Tech Support agent?"
Genie: "Brad Jones . . . "

Now, the telephone integration of the wireless communications system in accordance with the invention will be described in more detail.

A principle design goal of the wireless communications system is integration with the customer's telephone and voice mail systems in a manner that is as seamless as possible. By "seamless", we mean that the functionality enjoyed by badge users in badge-to-badge communication is also available—and works in exactly the same way—when some or all of the participants connect to the system through an ordinary telephone. Seamless integration also entails that the customer's voice mail system, if any, is accessible smoothly.

Seamless integration is difficult to attain not only because of the intrinsic differences between phones and badges, but also because PBX and key telephone systems—especially digital ones—are not well standardized; nor do there exist standard control interfaces to voice mail systems. Worse, individual vendors typically do not publish their proprietary API's. These difficulties are compounded by the lack of a single main supplier. Fortunately, the majority of interoperability features one could imagine supporting can be implemented by connecting to the customer's telephone equipment through standard analog (POTS) lines. Telephone system vendors offer modules that can be installed in their key or PBX systems that provide some number of analog ports. The hardware aspects of this feature are described above with reference to FIG. 6.

The telephony integration may include incoming calls and outgoing calls. In particular, calls originating from the outside are placed to a phone number dedicated to the wireless communications system. Depending on the customer's system, the number might be a PBX extension, or a directly dialed number. The wireless communications system number will typically be set up as part of a hunt group, allowing a single phone number or extension to support multiple lines. The incoming call is greeted with a voice dialog in which the caller is asked to say the name, or alternatively, to enter an extension number, of the user to whom the call is to be routed. The call is then handled much in the same manner as would be the case were the call placed from a badge. Note, however, that the initial interaction needs to be more regimented, because the caller cannot be assumed to be a user of the system. In particular, the caller is limited to contacting another user.

It may be useful to provide a special pass code that the caller could enter (via the telephone keypad) to reach the usual Genie. He would first be asked to speak his own name; assuming it was recognized, he would then hear the Genie prompt as if he had hailed the Genie from his badge. If Caller ID identified the source number as the cell phone number of the user, for example, the pass code and initial dialog could be bypassed altogether. This would enable a user to reach the Genie with a single press of a speed-dial button on his cell phone. From the point of view of the user receiving the call, it is very much as if the call originated from another badge. In particular, all of the following features are supported, in all of variations that are normally available:

Call Forwarding
Leaving a Message
Call Transfer
Call Waiting
Conferencing
Hold
Conferencing Additional Parties
Caller ID (when available)

For an outgoing telephone call from the wireless communications system, calls can be placed through the public phone system using the "Dial" voice command. For example, Mary might hail the Genie and say, "Dial area code six-five-oh eight-five-one-two-two-three-four". If an outsider has been set up as a buddy, a buddy name could be provided to the "Call" command, as in, "Call Mom". Supported features include most of those available when calling another badge:

Call Transfer
Call Waiting
Conferencing
Hold
Conferencing Additional Parties

In some customer environments, it is desirable to restrict placement of outgoing calls to certain privileged users, such as managers. Selective enabling of outside calling is available from the User Administration page of the administration application. Now, the display unit on the badge will be described in more detail.

The LCD display on the back of the badge displays incoming call information, messages, and status information of various kinds. The display is manipulated through a menu system controlled by the group of three pushbuttons at one edge of the badge. These will be referred to as the up button (topmost), the down button (lowermost), and select button (middle). The function of the outer two is context dependent. When a conversation is in progress, they control speaker volume; when menus are active, they provide scroll up and scroll down functions. The middle button is used to make menu selections from the display. Through the menu system, a user can set the speaker volume level, peruse text messages, power the badge off, and examine various attributes of the badge, such as its ID number. The functions of the display and the associated controls depends on which mode the badge is in at the time as will now be described in more detail.

Powered Off

In this mode, the unit is completely inactive, and the display is blank. Pressing the activate button at this point brings the badge back to life, displays a welcome message, "Hello, Dave", and enters Standby Mode. The unit can be restored to the Power Off mode via a menu selection.

Standby Mode

The Standby mode is one in which the unit is powered on, but no conversation is active, and in which the user is not currently interacting with the menus. The display shows the Home screen, which exhibits the name of the user to whom the badge is currently assigned. Status icons at the top of the screen show battery level, signal strength (if currently within the network neighborhood), and an indication of the presence of new (i.e., unread) messages. The user can transition to Active mode by pressing the activate button to hail the Genie (if currently within the network neighborhood). Similarly, a transition is made to Active mode in the event of an incoming call. Pressing any of the select, up or down buttons effects a transition to Menu mode.

Activated Mode

In this mode, a conversation is taking place either with the Genie or with other parties. The display continues to show the Home screen, and the screen flashes the name of the calling party (or "Vocera", if speaking to the Genie). Pressing the up or down buttons in this mode adjusts the volume level correspondingly. The display shows a graphic indicating the new level momentarily. Pressing the select button in this mode effects a transition to menu mode, thus allowing interaction with the menus (to peruse a message, for example) while a conversation is in progress. When the conversation ends (because, for example, the user presses the activate button), the badge reverts to Standby mode.

Menu Mode

In this mode, the user can interact with the LCD display for various purposes. The menu mode is entered by pressing either the up or the down button when in the Standby mode. The mode is not available while a call is in progress; instead, pressing the up or down buttons while in Active mode directly controls volume. Once in Menu mode, the various menu functions can be navigated and selected by means of the up, down, and select buttons. The mode can end in a number of ways. First, a press-and-hold of the select button will always return the badge to Standby. Menu mode may also end as a result of the initiation of a call (by pressing the activate button) or in the event of an incoming call. The badge may also return to Standby by virtue of certain menu selections. For example, if the select button is pressed while looking at the Info screen, it is assumed that the user is done examining that screen and the badge returns to Standby. Now, an example of a preferred menu organization in accordance with the invention will be described.

FIG. 11 illustrates an example of a preferred menu organization for the badge in accordance with the invention. In particular, the menu may include a home screen 300, a messages screen 302, a volume screen 304, a power off screen 306 and an info screen 308 as shown. The menu functions are accessed from a set of four selection screens, each of which has a text label and an icon suggesting the function that appear on the display. Initially, the user is presented with the home screen 300 and a user can navigate through these selection screens by pressing the up and down buttons on the badge. In a preferred embodiment, the visual effect is that of rotating through them as if they were arranged on a wheel. By navigating past the last screen in the rotation, one comes back to the Home screen as shown in FIG. 11. If one uses, say, the down button rather than the up button, the screens are traversed in the reverse order. Once the selection screen of interest is in view, the user pushes the select button to make the choice. What happens next depends on the selected function.

The message screen 302 may be selected and a scrolled list of subject lines are displayed to the user (shown as the message list 310 which displays each message text 312 as shown). Each line displays the subject of a message, preceded by an icon indicating whether the message is new (i.e., unread). If the subject is too long to fit on the line, it is simply truncated. The user navigates the list of subjects using the up and down buttons (causing each line to be highlighted in reverse video in a preferred embodiment), and selects a message to be displayed with the select button. The displayed message is headed by a Date line, a From line, and a Subject line. The Date line gives the date and time the message was received; the From line gives return address of the message, if known. The Subject line gives the full text of the subject. The message body itself then follows the header as is well known. The user can scroll though the displayed message using the up and down buttons. Note that the header lines are part of the scrolled text, and so may be word-wrapped if long enough to exceed the number of characters (approximately 14) that may be shown on a single line. When the user has finished examining the message, he can press the select button to return to the subject list, and choose another message to read. Alternatively, he can press and hold the button to return to Standby mode.

If the user presses the select button while viewing a message, a pop-up menu is displayed showing the following options:

Delete—This selection brings up a confirmation submenu prompting the user to confirm the deletion ("Delete" or "Cancel"). If confirmed, the message is deleted and the message list is redisplayed. Note that if a user has elected the "Save Messages" option in the User Console, the message will be "beamed up" to the server and archived whether it is deleted or not.

Reply—This selection brings up a submenu allowing the user to reply to the message with one of the Predefined Text Messages configured in the User Console. The submenu has an item for each such message; depending on the length of the message, it may show only the first several characters. Selecting one of the items brings up a confirmation submenu ("Send" or "Cancel"). Selecting either of these displays a confirm message momentarily, then returns to the Message List.

Save—This selection archives the message so that it will not be automatically deleted.

Cancel—Returns to the Main Menu.

Exit—Exits the menu system altogether.

The volume screen 304 may be selected and displays a screen with a graphic representation of the current speaker volume level in a volume control page 314. By pressing the up and down buttons, the user can adjust the volume wherein each button press plays a tone to provide audible feedback to the user of the currently set volume level. The press of the select button finalizes the interaction, and the badge is brought back to Standby mode. The volume setting is retained in flash memory so that it is retained even when power is not being supplied to the badge.

The power off screen 306 blanks the display, and places the badge in a low power state. The badge can subsequently be turned back-on simply by pressing the activate button. The powering down of the badge does not cause the loss of any settings or messages (since these are stored in a non-volatile memory) that may be stored in the badge. The info screen 308 may be selected and displays a info screen 316 to the user showing various information about the badge. Among the items shown are:

Badge IP Address

MAC address of the badge

Firmware version no.

Name of the network (Service Set ID)

Current Location (AP location name and MAC Address)

Radio Signal Quality

Name of Logged in User

Server IP Address

Each of the items of information is displayed full screen; the up and down buttons move among the various items.

FIG. 12 is a the menu state transition table 320 which details transitions among the various menu states. A column 322 at the left lists the various screens. The entries 324 to the right of each screen name give the screen transitioned to or action taken as a result of pushing the various buttons represented across the top of the table (including the Up button, the Down button, the Select button and the Select and Hold action). For example, starting from the Home screen, one arrives at the Info selection screen by pressing the down button. Entries shown in italics represent actions within the same screen (such as Scroll Up which indicates that the action is to scroll up in that screen). The select and hold action always returns the display to the Home screen as shown. Now, a summary of the voice commands in a preferred embodiment of the system will be described.

This summary is a listing of the badge voice commands, together with examples of use. In some cases, a command may have several syntactic variations, including synonyms. In these cases, a representative (but not necessarily complete) sampling of variations is given. Generally speaking, the number of synonyms a command has is proportional to its frequency of use. The Call command, for example, has several variants, as do "Yes" and "No" answers to confirmation dialogs. Unless otherwise noted, it can be assumed that a command that takes the name of a user as an argument will also work if multiple names (or group names) are provided.

Accept—Accepts calls from one or more parties.
"Accept all calls"
"Accept all calls from Jack"
"Accept all calls except from Marketing"
"Accept calls only from Marketing"
"Accept calls from Marketing only"
"Accept calls from everyone"
"Accept calls from buddies"

Add to Group—Dynamically adds a user to a group.
"Add me to Tech Support"
"Add me to group Tech Support"

Assign Location—Assigns the currently-associated access point to a location
"Assign location 'First Floor'"

Begin Tour—Begins access point location tour.
"Begin Tour"

Block—Blocks calls from one or more parties.
"Block all calls"
"Block all calls from Jack"
"Block all calls except from Marketing"
"Block calls only from Marketing"
"Block calls from Marketing only"
"Block calls from everyone"
"Block calls from buddies"

Call—Places a call to one or more parties.
"Call Mary"
"Find Mary"
"Get me Mary"
"Contact Mary"
"Call Mom"

Cancel (Universal)—Cancels current action.
"Cancel"
"Stop"
"Wait"

Conference—Conferences one or more parties.
"Conference Jack and Jill"

Delete—Deletes messages.

Dial—Dials a phone number
"Dial four-oh-eight seven-nine-oh-forty-one-hundred"
"Dial area code four-oh-eight seven-nine-oh-forty-one-hundred"
"Dial extension three-five-four"
"Dial nine-one-one"
"Phone nine-one-one"

End Tour—Ends access point location tour
"End Tour"

Erase Greeting—Erases current greeting.
"Erase greeting"
"Erase my greeting"
"Delete my greeting"

Forward—Forwards unanswered calls to a user, group, voicemail or phone
"Forward calls to my desk phone"
"Forward calls to my cell phone"
"Forward calls to voicemail"
"Forward calls to my home phone"
"Forward calls to my home phone"
"Forward calls to Sandy Flores"
"Forward calls to extension 101"

Goodbye—Dismisses Genie
"Goodbye"

Help (Universal)—Offers help for the current voice command.
"Help!"

Invite—Invites a newcomer to an ongoing conversation
"Invite Joe Smith"

Learn Name—Trains the Genie on a particular name.
"Learn a Name." The Genie then responds with "Spell the last name of the person you would like me to learn . . . "

Locate—Locates members of a group.
"Locate tech support reps in Building C"
"Locate the closest tech support agent"

Log Off—Un-assigns the badge.
"Log off"
"Log me out"

Log On—Assigns the badge to a user.
"Log me in as Mary Smith"
"Log me on as Mary Smith"

My Location Is—Binds access point location name.
"My location is Third Floor West Wing"

Play Greeting—Plays back previously-recorded greeting
"Play greeting"
"Play my greeting"

Play Messages—Plays messages left by other users.
"Play messages"
"Play old messages"
"Play messages from John"
"Play back my old messages from John"

Record E-Mail—Sends an e-mail with a voice message to one or more users.
"Record e-mail for the Blowtorch team"
"Send e-mail to Jack"

Record Greeting—Records greeting for a given user.
"Record greeting"
"Record my greeting"

Record Message—Broadcasts a voice message to one or more users.
"Record a message for John"
"Send message to the John"
"Leave a message for John"
"Leave an urgent message for John"
"Message for John"
"Urgent message for John"

Record Name—Records a name prompt for a person, group or location.
"Record my name"
"Record name for John Smith"
"Record name for Tech Support"
"Record name for the First Floor"

Remove from Group—Dynamically removes a user from a group.
"Remove me from Tech Support"
"Remove me from group Tech Support"
Stop Forwarding—Ends forwarding of unanswered calls.
"Stop Forwarding"
Transfer—Transfers current call to another user or to voice mail.
"Transfer to John Smith"
"Transfer to voice mail"
What Groups—Lists groups to which member belongs
"What groups do I belong to?"
"What groups am I a member of?"
Where Is—Locates a user
"Where is Mary?"
"Find Mary"
Who Am I—Asks to which user the badge is assigned.
"Who am I?"
Who is in group—Asks to enumerate the members of a given group
"Who is in Tech Support?"
Where Am I—Asks for the user's current location.
"Where am I?"
Who Called—Asks who called or left a message.
"Who called?"
"Who called me?"
Who is in group?—Lists the members of a group
"Who is in Marketing?"
"Who is in group Tech Support?"
Who Is Blocked—Plays back names of users who are blocked
"Who is blocked?"

While the foregoing has been with reference to a particular embodiment of the invention, it will be appreciated by those skilled in the art that changes in this embodiment may be made without departing from the principles and spirit of the invention, the scope of which is defined by the appended claims.

The invention claimed is:

1. A system for locating a user of a wireless communications system wherein the wireless communications system has a central computer connected to one or more access points which communicate wirelessly with a badge associated with a user, the system comprising:

a badge having a microphone that accepts a voice-based locate command;

means for determining, based on the voice-based locate command, the current access point being used for communications by the badge of the user being located; and means for generating a location indicator for the user wherein the location indicator is the name and location of the access point currently being used by the user.

2. The system of claim 1, wherein the name of the access point further comprises one of a building name, a floor name and a functional area name.

* * * * *